(12) United States Patent
     Lotfi

(10) Patent No.: US 9,263,172 B2
(45) Date of Patent: Feb. 16, 2016

(54) WIRE CONSTRUCTS

(75) Inventor: Atoosa Lotfi, Valencia, CA (US)

(73) Assignee: ADVANCED BIONICS AG, Staefa (CH)

( * ) Notice: Subject to any disclaimer, the term of this patent is extended or adjusted under 35 U.S.C. 154(b) by 260 days.

(21) Appl. No.: 13/985,237

(22) PCT Filed: Feb. 16, 2012

(86) PCT No.: PCT/US2012/025485
§ 371 (c)(1),
(2), (4) Date: Aug. 13, 2013

(87) PCT Pub. No.: WO2012/154256
PCT Pub. Date: Nov. 15, 2012

(65) Prior Publication Data
US 2013/0333918 A1    Dec. 19, 2013

Related U.S. Application Data

(60) Provisional application No. 61/443,814, filed on Feb. 17, 2011, provisional application No. 61/521,664, filed on Aug. 9, 2011.

(51) Int. Cl.
| H01B 7/00 | (2006.01) |
| H01B 7/04 | (2006.01) |
| A61N 1/05 | (2006.01) |
| B23K 26/08 | (2014.01) |
| B23K 26/20 | (2014.01) |
(Continued)

(52) U.S. Cl.
CPC .............. *H01B 7/048* (2013.01); *A61N 1/0541* (2013.01); *B23K 26/0823* (2013.01); *B23K 26/20* (2013.01); *B23K 26/367* (2013.01); *B23K 26/4075* (2013.01); *B29C 47/003* (2013.01); *B29C 47/8805* (2013.01); *A61N 1/0551* (2013.01); *B23K 2201/32* (2013.01); *B23K 2201/38* (2013.01); *B29C 37/0053* (2013.01); *B29K 2083/00* (2013.01); *H01B 13/0013* (2013.01)

(58) Field of Classification Search
USPC ...... 174/110 R, 113 R, 117 R, 117 F, 117 FF, 174/155, 116, 112
See application file for complete search history.

(56) References Cited

U.S. PATENT DOCUMENTS 3,082,292 A * 3/1963 Gore .......................... 174/117 F
3,239,396 A * 3/1966 Bohannon, Jr. ................. 156/52
(Continued)

FOREIGN PATENT DOCUMENTS

CA    2533215    5/2012
EP    0109222    5/1984
(Continued)

*Primary Examiner* — William H Mayo, III
(74) *Attorney, Agent, or Firm* — Fabian Vancott; Steven L. Nichols

(57) ABSTRACT

A method for forming a wire construct includes forming a groove in a polymer having a mouth that is narrower than a width of a deeper portion of the groove and placing a substantial length of wire in the groove, the wire having a larger cross-sectional dimension than the mouth of the groove. Encapsulant is placed over the polymer. The wire construct is to be used for implantable stimulation leads, such as a cochlear stimulation lead or a neurostimulation lead. Two wire constructs can be assembled to form a multilayer wire construct.

22 Claims, 22 Drawing Sheets

(51) Int. Cl.
    *B23K 26/36*     (2014.01)
    *B23K 26/40*     (2014.01)
    *B29C 47/00*     (2006.01)
    *B29C 47/88*     (2006.01)
    *B29C 37/00*     (2006.01)
    *B29K 83/00*     (2006.01)
    *H01B 13/00*     (2006.01)

(56) References Cited

U.S. PATENT DOCUMENTS

| | | | | |
|---|---|---|---|---|
| 3,622,687 | A * | 11/1971 | Doughty | 174/97 |
| 3,663,739 | A * | 5/1972 | Chevrier | 174/36 |
| 3,818,122 | A * | 6/1974 | Luetzow | 174/86 |
| 4,321,425 | A * | 3/1982 | Emmel | 174/32 |
| 4,538,024 | A * | 8/1985 | Wise et al. | 174/117 F |
| 4,626,298 | A * | 12/1986 | Allard | 156/55 |
| 4,845,311 | A * | 7/1989 | Schreiber et al. | 174/36 |
| 5,360,944 | A * | 11/1994 | Springer et al. | 174/117 F |
| 5,373,109 | A * | 12/1994 | Argyrakis et al. | 174/117 FF |
| 5,665,809 | A | 9/1997 | Wojtowicz | |
| 5,720,099 | A | 2/1998 | Parker et al. | |
| 6,043,434 | A * | 3/2000 | Prudhon | 174/113 R |
| 6,222,131 | B1 | 4/2001 | Schilson | |
| 6,374,143 | B1 | 4/2002 | Berrang et al. | |
| 6,631,559 | B2 * | 10/2003 | Ueno | 29/861 |
| 7,256,345 | B2 * | 8/2007 | Inoue | 174/36 |
| 7,267,552 | B2 * | 9/2007 | Lin et al. | 439/67 |
| 7,968,796 | B2 * | 6/2011 | Chang et al. | 174/117 F |
| 2004/0147825 | A1 | 7/2004 | Milojevic et al. | |
| 2004/0147992 | A1 | 7/2004 | Bluger et al. | |
| 2004/0172118 | A1 * | 9/2004 | Gibson | 607/137 |
| 2004/0220651 | A1 | 11/2004 | Kuzma et al. | |
| 2005/0016657 | A1 * | 1/2005 | Bluger | 156/50 |
| 2008/0140156 | A1 | 6/2008 | Rodriguez et al. | |
| 2008/0288036 | A1 | 11/2008 | Greenberg et al. | |
| 2010/0023102 | A1 | 1/2010 | Spruit | |

FOREIGN PATENT DOCUMENTS

| | | |
|---|---|---|
| EP | 0938099 | 8/1999 |
| WO | 2005007235 | 1/2005 |
| WO | 2010099158 | 2/2010 |

* cited by examiner

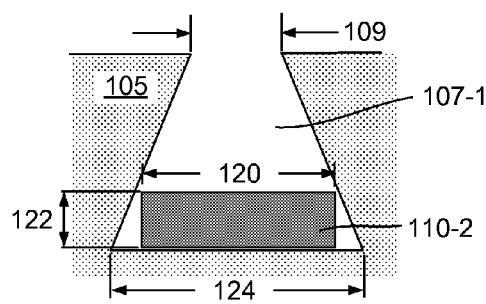
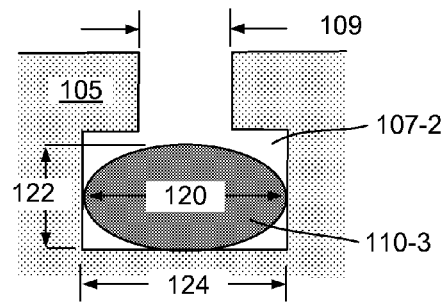
Fig. 1D  Fig. 1E
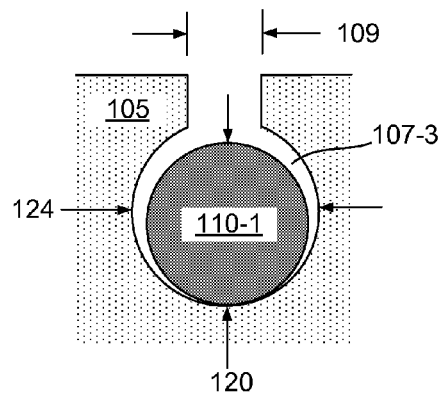
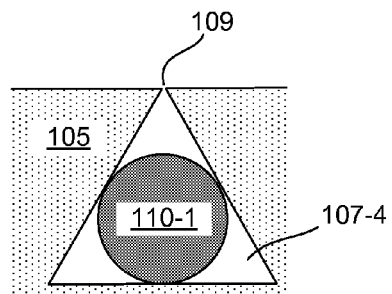
Fig. 1F  Fig. 1G

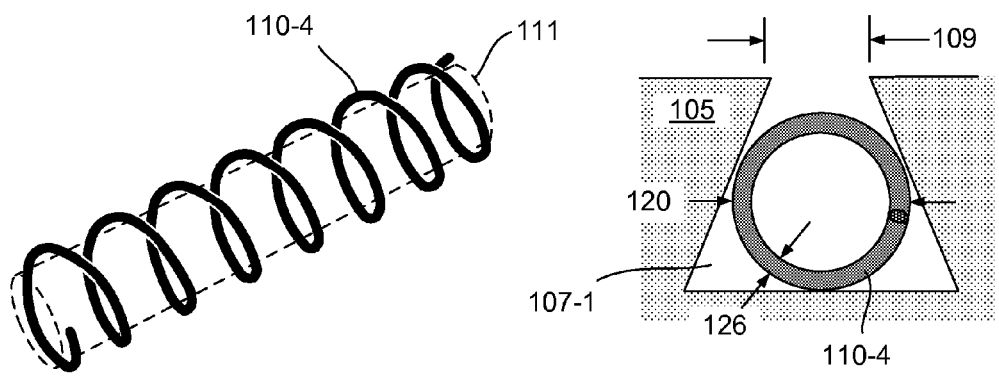
Fig. 1H  Fig. 1I
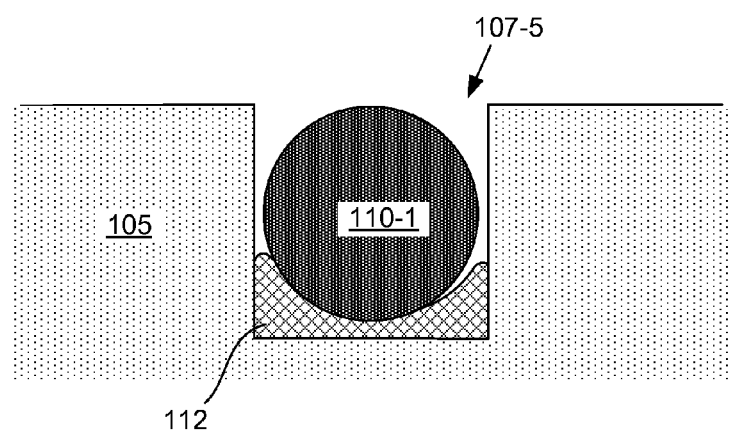
Fig. 1J

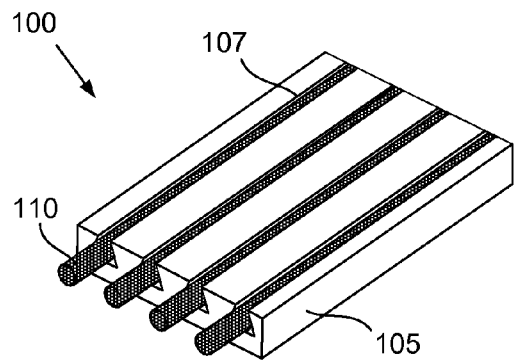
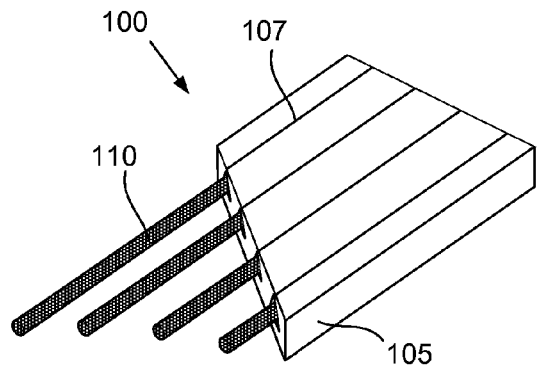
Fig. 2A  Fig. 2B
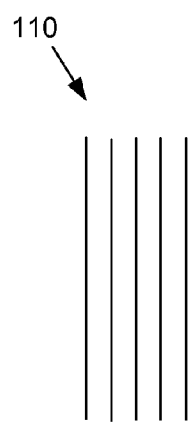
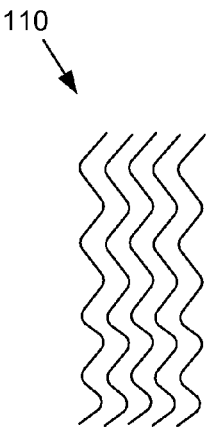
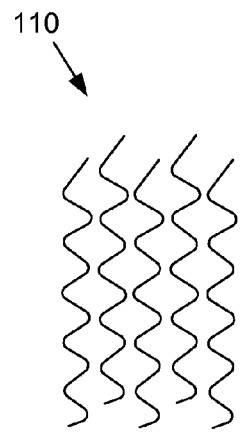
Fig. 2C  Fig. 2D  Fig. 2E

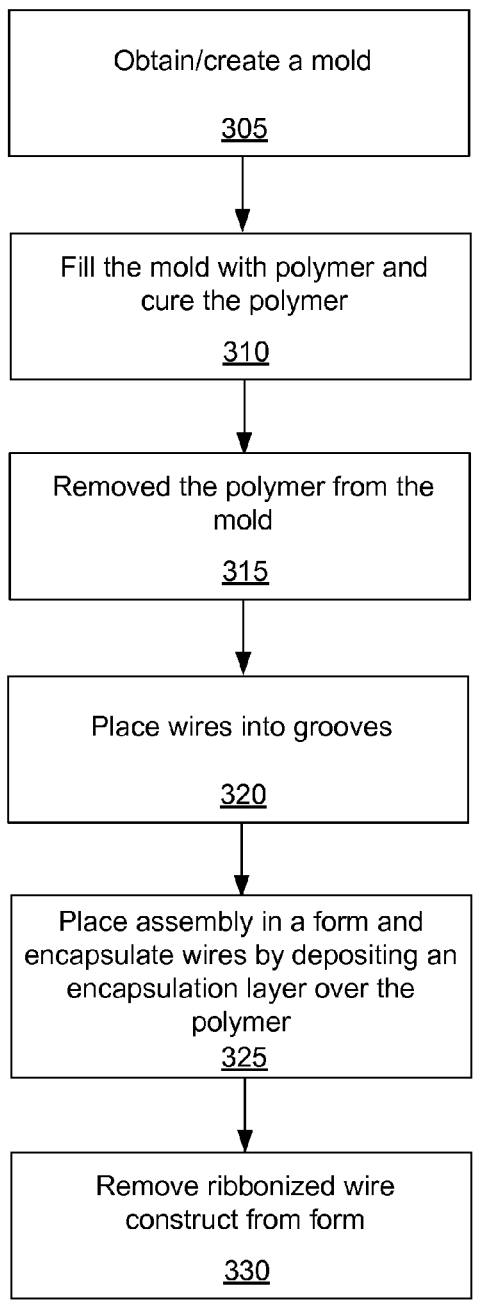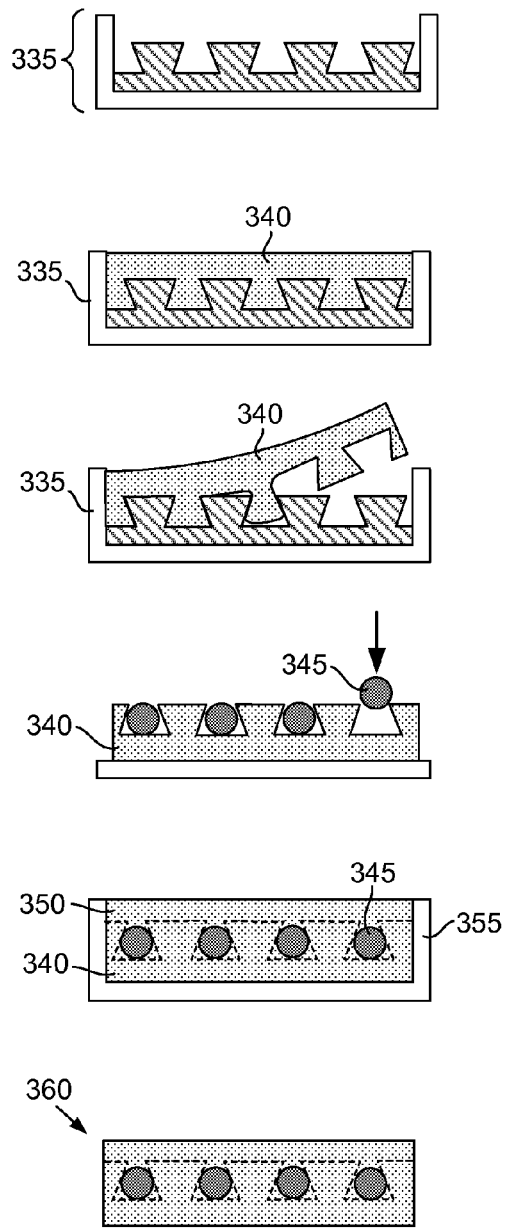
Fig. 3

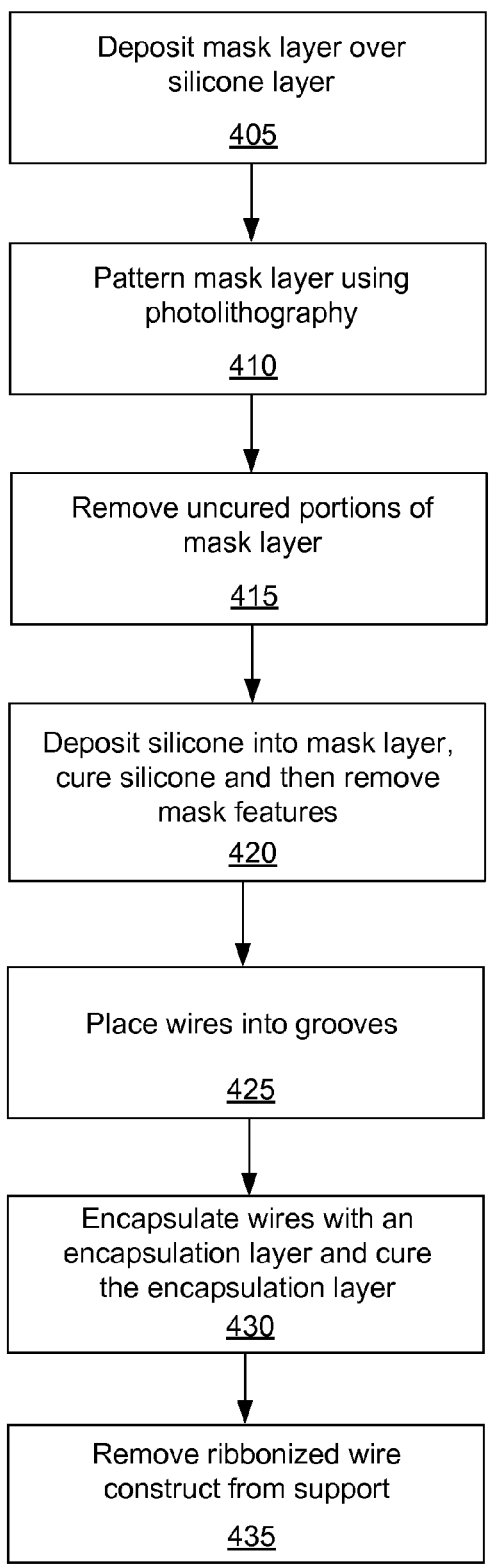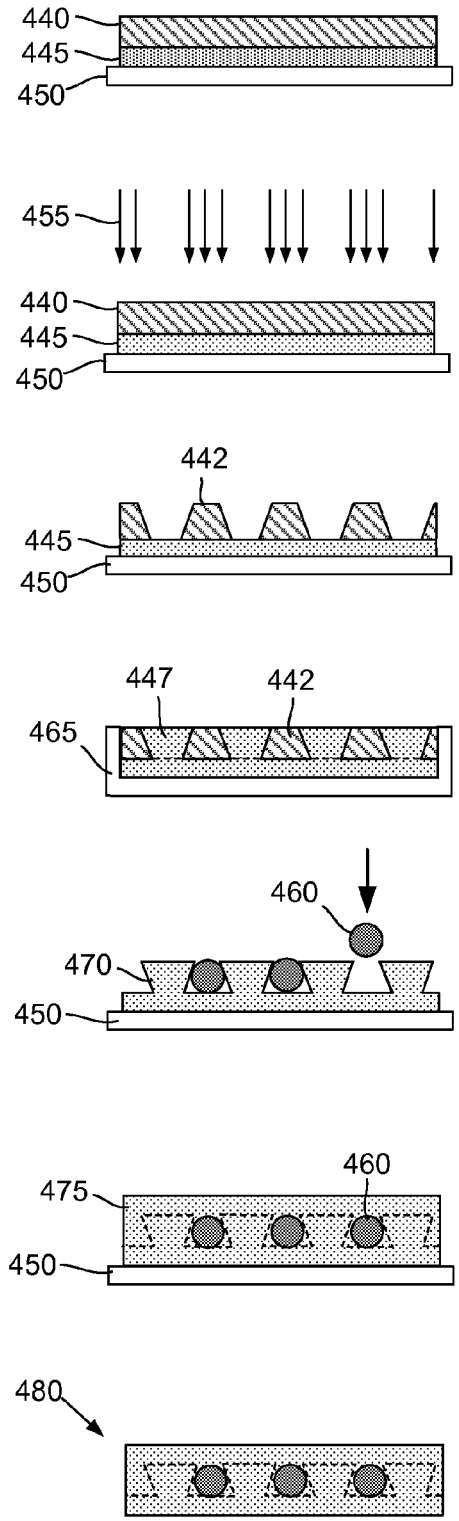
Fig. 4

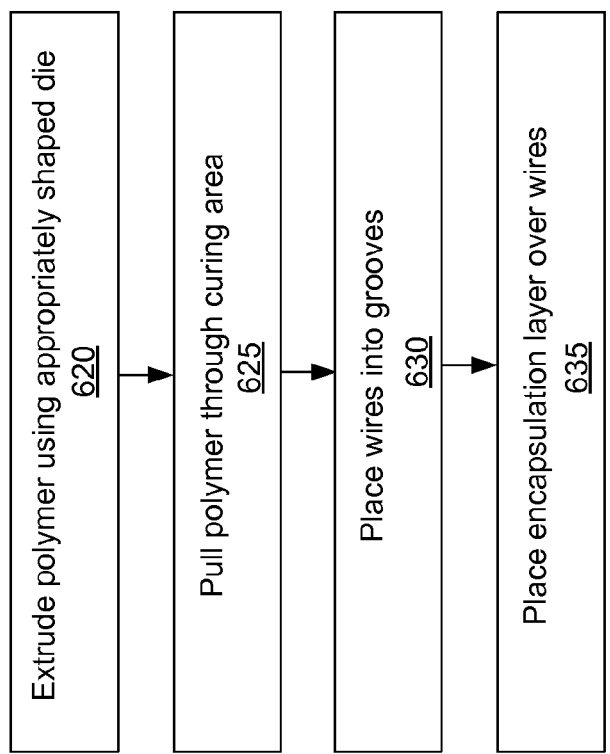
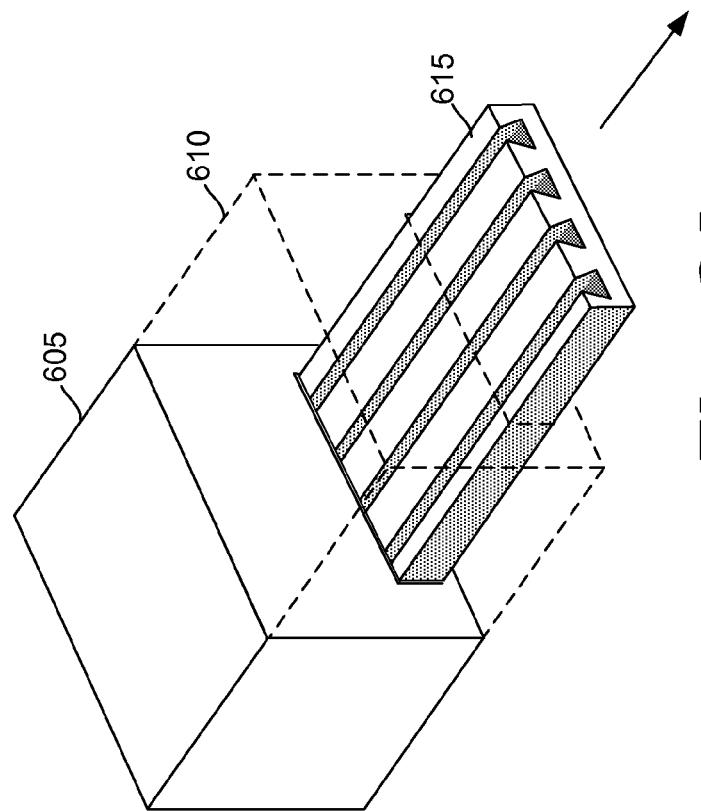

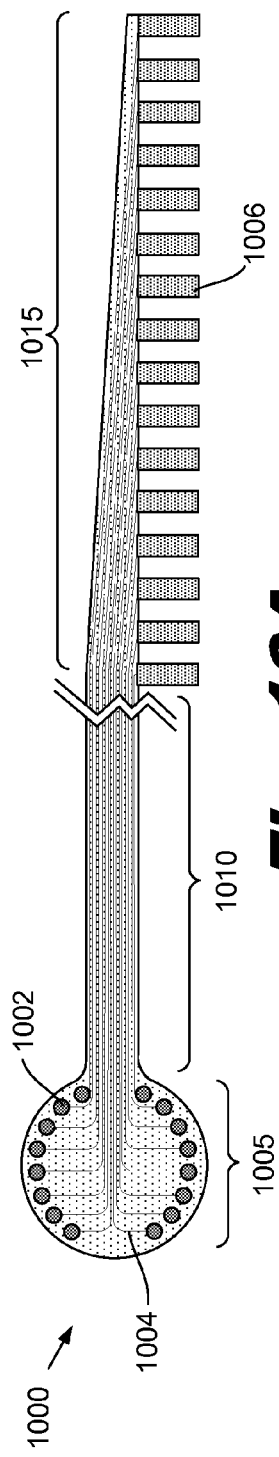
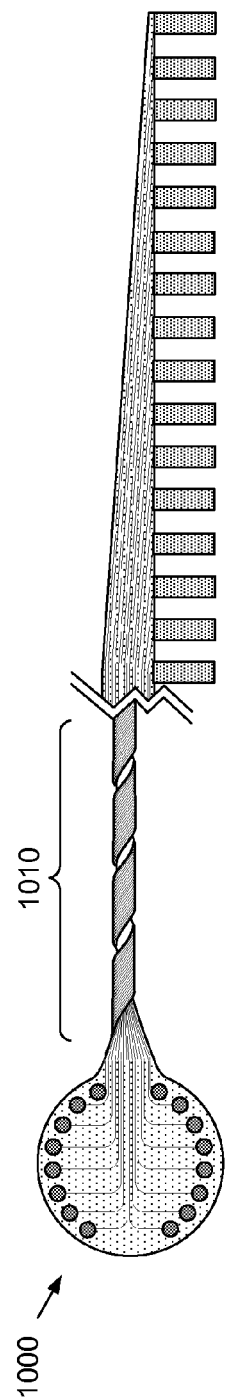
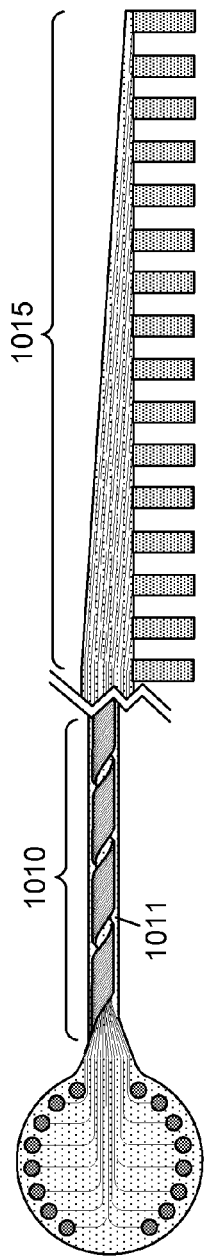

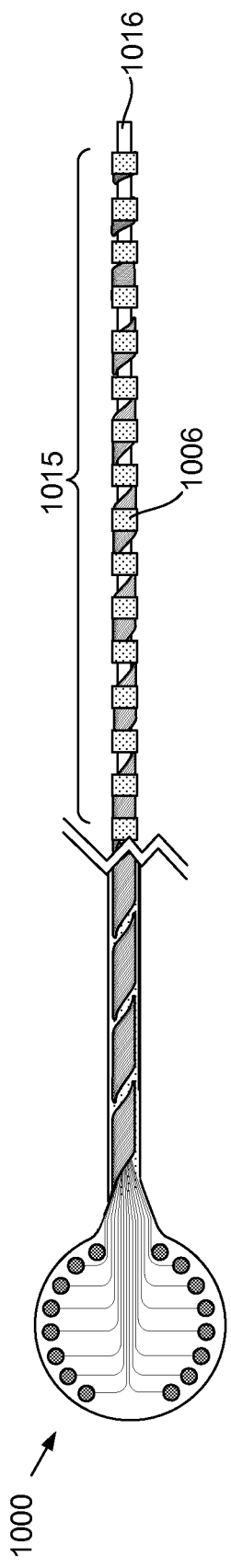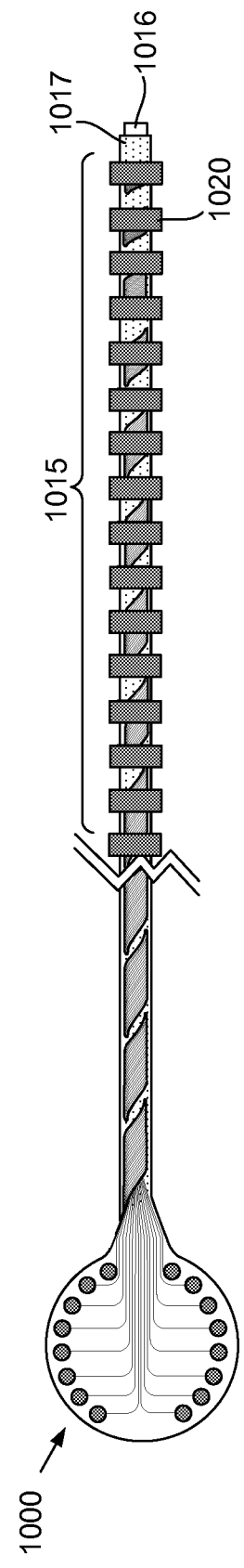

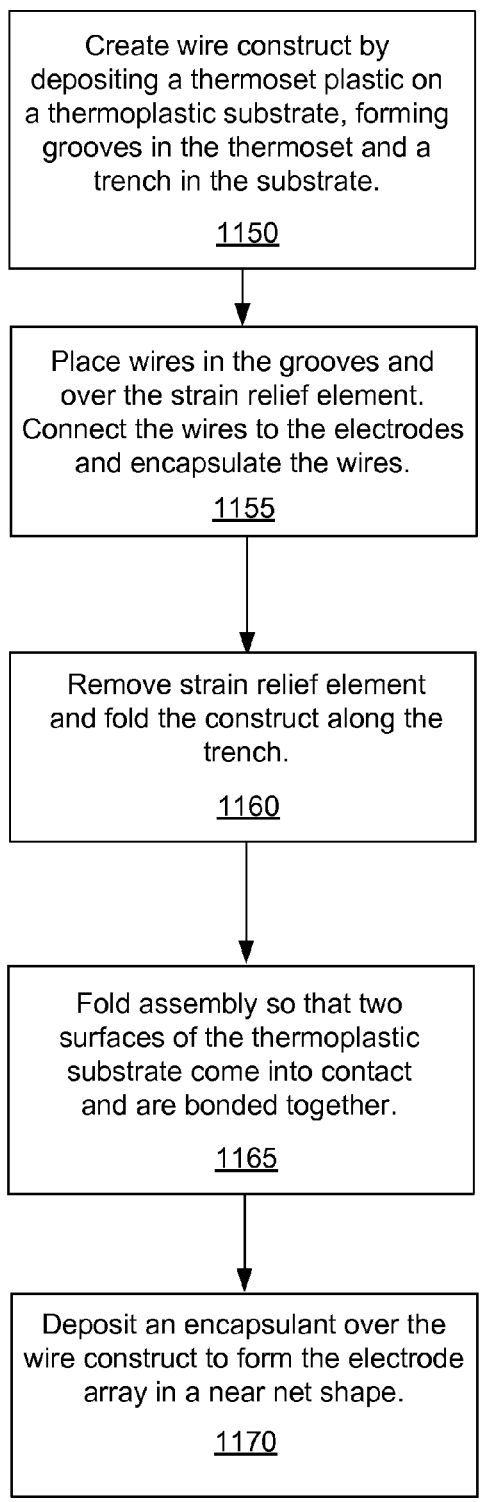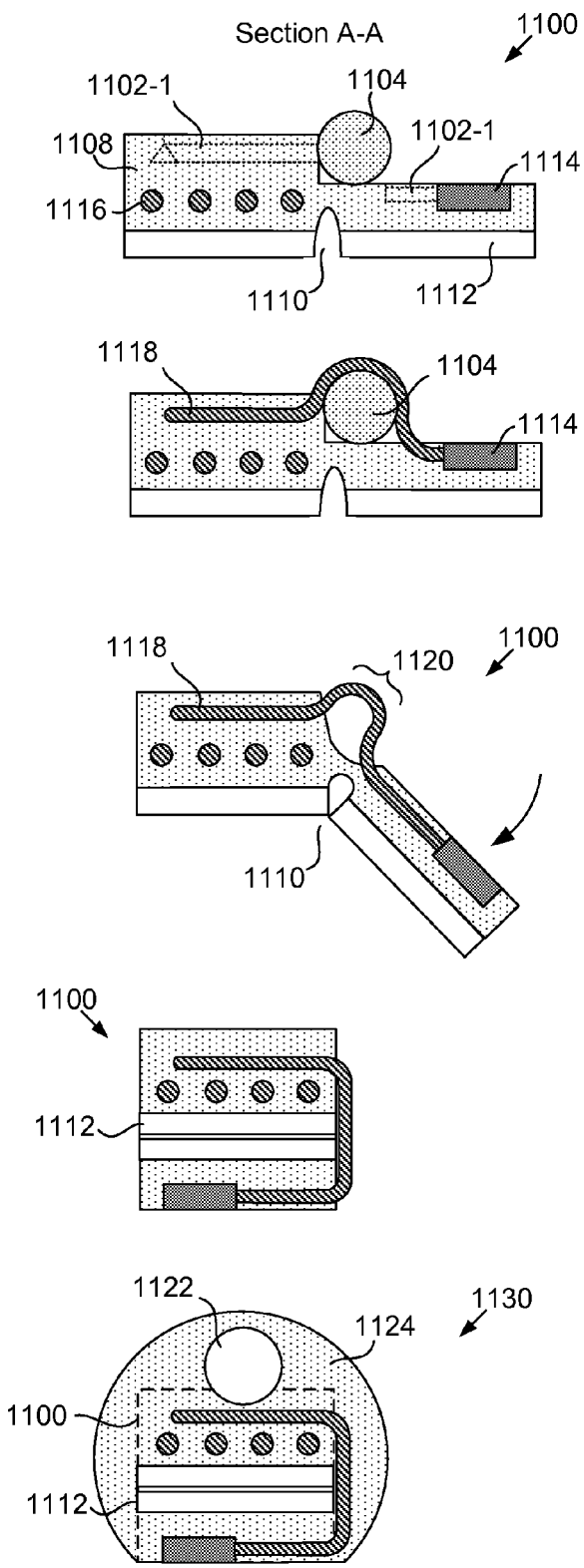
Fig. 11B

WIRE CONSTRUCTS

RELATED DOCUMENTS

The present application claims the benefit under 35 U.S.C. §371 to International PCT application No.: PCT/US2012/025485 filed Feb. 16, 2012 which claims the benefit under 35 U.S.C. §119(e) of U.S. Provisional Application No. 61/521,664 filed on Aug. 9, 2011, entitled "Wire Constructs" to Atoosa Lotfi and U.S. Provisional Application No. 61/443,814, filed on Feb. 17, 2011, also entitled "Wire Constructs" to Atoosa Lotfi. These applications are hereby incorporated by reference in their entireties.

BACKGROUND

Neurostimulating devices stimulate nerves by applying an electrical current. Such devices often include a biocompatible wire construct that carries current from a pulse generator or radio frequency (RF) link to the stimulation site. These wire constructs can include multiple small diameter wires and are typically constructed manually. Manually handling the wires is laborious and requires skilled technicians. This manual assembly process can result in significant variation in the spacing and organization of the wires that make up the wire construct. This can lead to undesired variations in the geometry and properties within and between wire constructs. Additionally, the manual manufacturing can be expensive because it is a low yield and a low throughput process.

BRIEF DESCRIPTION OF THE DRAWINGS

The accompanying drawings illustrate various embodiments of the principles described herein and are a part of the specification. The illustrated embodiments are merely examples and do not limit the scope of the claims.

FIGS. 1D-1G are diagrams of illustrative cross-sections of a flexible wire construct, according to one example of principles described herein.

FIGS. 1H-1I are a perspective view and a cross-sectional view, respectively, of an illustrative coiled wire that can be included in a flexible wire construct, according to one example of principles described herein.

FIG. 1J is a cross-sectional view of a wire adhered within a groove, according to one example of principles described herein.

FIGS. 2A and 2B are perspective views of illustrative flexible wire constructs, according to one example of principles described herein.

FIGS. 2C-2F are diagrams showing illustrative wire configurations within a flexible wire construct, according to one example of principles described herein.

FIG. 3 is a flowchart with associated cross-sectional diagrams of a method for forming an illustrative flexible wire construct that incorporates a molding process, according to one example of principles described herein.

FIG. 4 is a flowchart with associated cross-sectional diagrams of an illustrative method for forming a flexible wire construct that incorporates a photolithographic process, according to one example of principles described herein.

FIG. 6A is a diagram of an illustrative extrusion device for extruding a polymer with grooves, according to one example of principles described herein.

FIG. 6B is a flowchart of a method for forming a flexible wire construct using extrusion forming, according one example of principles described herein.

FIG. 10A-10G are diagrams of blocks to form a cochlear implant using flexible wire constructs, according to one example of principles described herein.

FIG. 11B is a flowchart of a method for construction of an electrode array, according to one example of principles described herein.

Throughout the drawings, identical reference numbers designate similar, but not necessarily identical, elements.

DETAILED DESCRIPTION

As discussed above, neurostimulating devices may include a biocompatible wire construct that carries current from a pulse generator or RF link to the stimulation site. These wire constructs can include very small diameter wires. For example, the wires in such a biocompatible wire construct may have a diameter measured in tens of microns. In many situations, the wire constructs are designed to be very flexible so that there is less stress on the electrical connections and the wire constructs are easier to maneuver into position in the biological environment.

Manually handling these miniature wires is laborious and requires skilled technicians. During this manual assembly process, there can be a significant variation in the spacing and organization of the wires that make up the wire construct. This can lead to undesirable variations in the geometry and properties within and between wire constructs. Further, the manual assembly process is not efficient in forming nonlinear wire paths. Nonlinear wire paths can substantially increase the longitudinal stretchability of the wire construct. Additionally, the manual manufacturing process is expensive because it is slow, involves significant human effort, and can result in a substantial amount of material waste.

According to one illustrative example, a wire construct can be formed by placing the wires into precision formed grooves in a polymer. The grooves hold the wires in place until the wires can be locked into place by an encapsulation layer. The grooves control the spacing and organization of the wires and can result in more predictable and accurate manufacturing. Further, many blocks in the process can be automated for a higher degree of precision and accuracy. This can result in a more rapid and cost effective process for manufacturing wire constructs for implantable applications. Increased process control can also lead to higher product reliability.

In the following description, for purposes of explanation, numerous specific details are set forth in order to provide a thorough understanding of the present systems and methods. It will be apparent, however, to one skilled in the art that the present apparatus, systems and methods may be practiced without these specific details. Reference in the specification to "an embodiment," "an example" or similar language means that a particular feature, structure, or characteristic described in connection with the embodiment or example is included in at least that one embodiment, but not necessarily in other embodiments. The various instances of the phrase "in one embodiment" or similar phrases in various places in the specification are not necessarily all referring to the same embodiment.

Figure 1A:
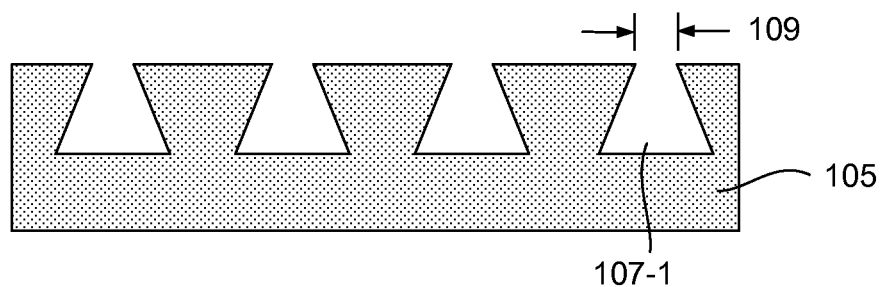
FIGS. 1A-1C are cross-sectional views of an illustrative flexible wire construct at various manufacturing stages, according to one example of principles described herein.
Figure 1B:
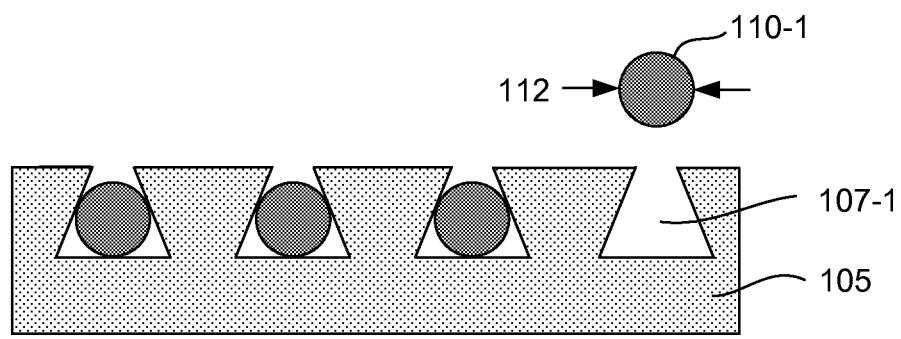
Figure 1C:
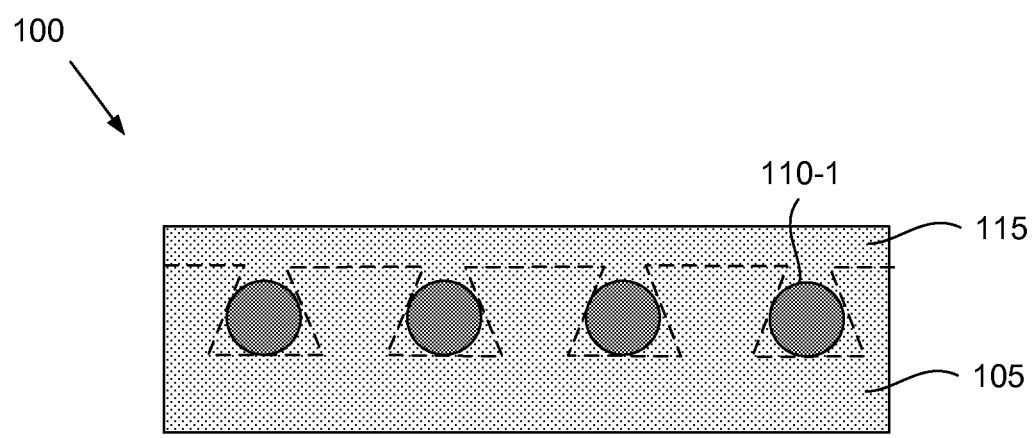

FIGS. 1A-1C are cross-sectional views of various manufacturing stages of an illustrative flexible wire construct. FIG. 1A shows a shaped polymer (105). The polymer (105) could be made from a number materials, including flexible thermoset polymers such as silicone. The shaped polymer (105) includes a number of grooves (107-1) that have a relatively narrow mouth (109) to a larger interior.

FIG. 1B shows a wire (110-1) placed in each of the grooves (107). As the wires (110-1) are pressed into the grooves (107), the larger diameter (112) of the wire (110-1) forces the narrow mouth (109) of the groove (107-1) open and then slides into the larger interior of the groove (107-1). The narrow mouth (109) closes or partially closes behind the wire (110-1) and secures the wire (110-1) into the groove (107-1). By using processes that precisely locate and form the grooves (107-1) in the polymer (105), the wires (110-1) are precisely located and spaced when they are captured by the grooves (107-1).

FIG. 1C shows a flexible wire construct (100) in which an encapsulation layer (115) has been deposited over the wires (110-1) and into the grooves (107-1) to encapsulate the wires (110-1). In some embodiments, the encapsulation layer (115) may not entirely encapsulate the wires (110-1) but is sufficient to hold them place in the grooves (107-1). The polymer (105) and the encapsulation layer (115) may be formed from the same or different materials.

FIGS. 1D-1G are cross-sectional diagrams of illustrative wire constructs. As used in the specification and appended claims, the terms "wire" or "wires" are used broadly and includes a wide variety of electrical conductors. For example, the wire may have a number of geometries including, but not limited to, round wire, flat wire, ribbon, foil, coiled wire, wire rope and braided cables. The wires may be formed from any biocompatible conductive material. For example, the wires may be formed from titanium, platinum, iridium, gold or alloys thereof. The wires may be bare or coated. For example, the wires may be coated with an electrically insulating fluoropolymer or parylene coating.

FIG. 1D shows a dovetail groove (107-1) formed in a polymer (105). For example, a dovetail groove may be an isosceles trapezoid or a triangle. In the embodiment shown in FIG. 1D, the widest portion (124) of the dovetail groove (107-1) is at the base of the groove. A rectangular wire (110-2) has been placed in the groove (107-1). The rectangular wire (110-2) has a width (120) that is greater than the width of the mouth (109), but less than the width of the widest portion (124). The thickness (122) of the wire (110-2) in this example is less than the width of the mouth (109).

FIG. 1E is a cross-sectional view of an oval wire (110-3) placed into a groove (107-2) with a rectangular geometry. The mouth (109) of the groove (107-2) is narrower than the width (124) of a deeper rectangular portion of the groove. The oval wire (110-3) has a width/major axis (120) and a thickness/minor axis (122). In this example, both the width (120) and the thickness (122) of the oval wire (110-3) are greater than the width of the mouth (109) of the groove (107-2).

FIG. 1F is a cross-sectional view of a wire (110-1) placed in a groove (107-3) that has a circular interior cavity and a narrower mouth (109). The wire (110-1) has a diameter (120) that is greater than the width of the mouth (109) but smaller than the cavity diameter (124).

FIG. 1G is a cross-sectional view of a round wire (110-1) that has been placed in a triangular groove (107-4). In this example, the triangular groove (107-4) is illustrated as an isosceles triangle. However, any appropriate geometry could be used, including other triangular, rectangular, circular, ellipsoid, irregular or polygonal shapes. The mouth (109) is almost entirely closed and forms a slit through which the wire (110-1) can be passed. The wire (110-1) can be inserted through mouth (109) in a number of ways including pressing the wire (110-1) through the mouth (109) or bending the polymer (105) to open the groove (107-4). Grooves (107-4) with closed geometries may have a number of advantages, including more securely holding the wire in place. Additionally, grooves (107-4) with closed geometries may also substantially prevent encapsulation material from entering the interior of the groove (107-4). Instead, the encapsulation layer may simply seal the mouth (109) shut to lock the wire (110-4) in the groove (107-4). This may allow the wire (110-4) to slide within the groove (107-4) as the wire construct flexes. Wire constructs that allow for motion of the wires can be significantly more flexible than wire constructs that restrict the relative motion of the wires.

FIGS. 1H-1I are a perspective view and a cross-sectional view, respectively, of an illustrative coiled wire (110-4) that can be included in a wire construct. In some examples, a temporary core (111) can be passed through the center of the coiled wire (110-4) to support and provide easier handling of the coiled wire (110-4). The temporary core (111) can be removed after the coiled wire (110-4) is placed within the dovetail groove (107-1).

The coiled wire (110-4) is made up of wire with a relatively small diameter (126), and the coil has a larger diameter (120) that is larger than the mouth (109) of the dovetail groove (107-1). There may be a number of advantages of using the coiled wire (110-4). For example, when encapsulated, the coiled wire (110) can provide greater longitudinal stretchability of the wire construct.

As illustrated in the figures above, the grooves (107) and wires (110) may have a variety of geometries. Each of the grooves (107) described above has a mouth (109) that is narrower than the width of a deeper portion of the groove. The wires have at least one cross sectional dimension that is larger than the width of the mouth (109) of the grooves. In some embodiments, the groove geometry is compatible with multiple types of wire cross-sections and vice versa.

FIG. 1J is a cross-sectional view of a polymer (105) with a rectangular groove (107-5). In this example, the mouth of the groove is not narrower than the other portions of the groove (107-5). Rather than relying on a narrow mouth to hold the wire (110-1) in place, adhesive (112) is deposited in the groove (107-5) or onto the wire (110-1). The adhesive (112) holds the wire (110-1) in place until the encapsulation layer locks the wire in place. The adhesive (112) can be made up of a number of materials, including uncured polymer that is later cured with the encapsulation layer.

FIG. 2A is a perspective view of an illustrative flexible wire construct (100) that shows the wires (110) and grooves (107) passing through the polymer (105) in a linear and parallel configuration. FIG. 2B is a perspective view of a wire construct (100) that has grooves (107) with a closed geometry similar to that shown in FIG. 1G.

FIGS. 2A and 2B show the ends of the wires extending from the polymer. This allows for connections to be made with the individual wires. The end of the polymer (105) can be cut, molded, or otherwise formed in any desired shape, including straight (as shown in FIG. 2A), angled (as shown in FIG. 2B), curved, or in any other desired configuration. Additionally, the wires (110) may extend at various lengths from the end of the polymer. In some examples, one or more wires may exit in the middle rather than the ends of the polymer. This provides more adaptability in making connections to the wire construct.

The linear arrangement of the wires shown in FIGS. 2A and 2B are schematically illustrated in FIG. 2C. There are a wide variety of other two dimensional and three dimensional arrangements of wires that can be formed within a polymer. These various arrangements of wires (110) can be selected to provide desired characteristics to the resulting wire construct (100). The use of grooves in a polymer to shape these wires can result in very uniform arrangements that would be very difficult to form manually. Where stiff wire is used, it may be advantageous to form the stiffer wire into the desired nonlinear shape prior to placing it into the grooves.

Figure 2F:
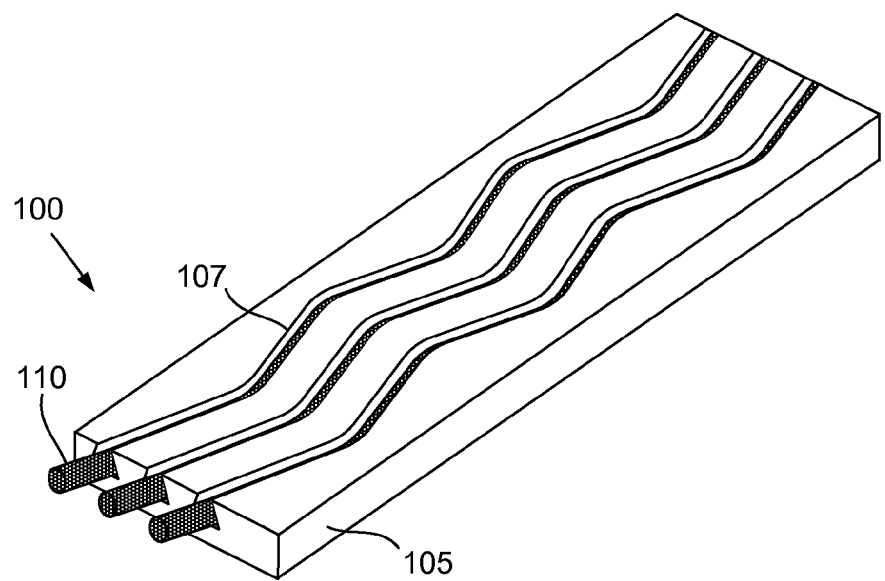

FIG. 2D is a schematic view of wires (110) that are generally parallel to each other but have a side-by-side sinusoidal configuration. FIG. 2E is a schematic view of wires (110) that are generally sinusoidal and are out of phase with adjacent wires. FIG. 2F shows a perspective view of wires (110) within nonlinear grooves (107) in a polymer (105). These nonlinear wire paths greatly increase the longitudinal stretchability of the wire construct (100). This may have a number of advantages. For example, an implant may be placed in a biological environment where there is some amount of dynamic motion. Additionally, the flexibility of the wire construct also facilitates atraumatically maneuvering of the implant into position in the body, especially when it is guided along a tortuous path or must conform to a curved surface. The flexibility along the length of the construct (100) can accommodate this motion without dislodging electrodes or generating undesirable strains on interconnections. This configuration could also accommodate growth related dimension changes without necessitating removal and replacement of the implanted device. For example, an implant may be placed in child. As the child grows, the distance between the stimulation site and the pulse generator may change. A wire construct with a substantial amount of extension flexibility can change length as the distance increases without creating a substantial amount of stress at the interconnections.

Figure 2G:
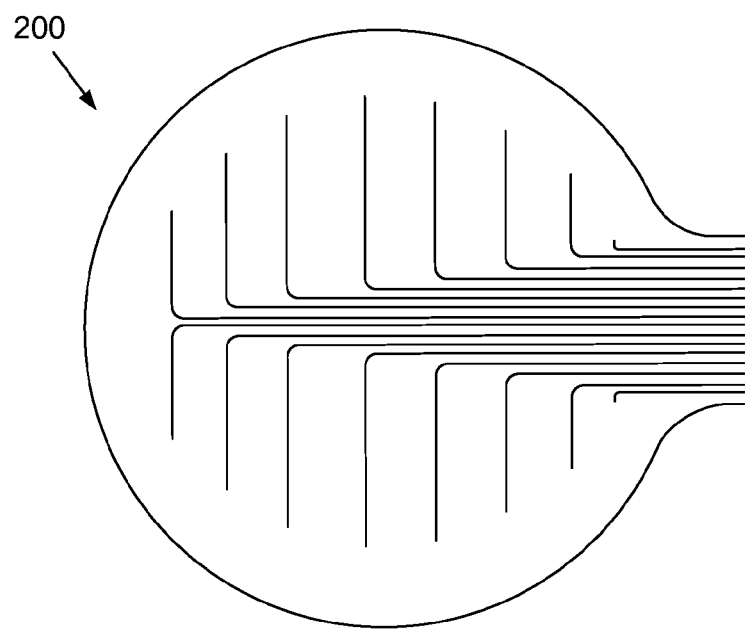
FIG. 2G is a top view of a flexible wire construct with nonlinear wire routing, according to one example of principles described herein.

FIG. 2G is a diagram of a flexible wire construct (200) that includes nonlinear wire routing. This flexible wire construct (200) could be used, for example, to distribute the wires to a ring of electrical contacts.

In some illustrative examples, the polymer (105) may be a silicone material. Silicone materials may have a range of mechanical properties. A silicone with the desired properties can be selected for a particular application. For example, a number of medical grade silicone elastomers are biocompatible, flexible, and can be shaped using a number of techniques including liquid injection molding, casting, bench top molding, extrusion, calendering, and other techniques. The flexibility of silicone can be advantageous when incorporating shape memory alloys and shape memory polymers into the wire construct. Shape memory materials change their shape in response to an external variable. For example, some shape memory alloys and polymers change their shape in response to changes in temperature. Consequently, a flexible silicone wire construct could include a shape memory material that has a first shape at room temperature and a second shape at body temperature. As the wire construct is inserted into the body, the temperature of the wire construct also increases. This can cause the shape memory material to change shape and influence the overall shape of the flexible silicone wire construct.

In general, the method for forming flexible wire constructs includes providing a polymer and forming at least one groove in the polymer with a mouth that is narrower than a width of a deeper portion of the groove. A substantial length of a wire which has a larger cross-sectional dimension than mouth of the groove is placed in the groove. The groove holds the wire in place until an encapsulant is deposited over the polymer. FIGS. 3, 4, 5A-5B, 6A-6B, and 7 are specific, non-limiting examples of systems and methods which could be used to create flexible wire constructs.

FIG. 3 is flowchart with associated cross-sectional diagrams of a method for forming an illustrative flexible wire construct that incorporates a molding process. A variety of flexible polymers could be used in this method. These flexible polymers are elastic enough to pull out from the large undercuts used in this molding process. The flexible polymer may include flexible thermoset polymers. In embodiments described below, medical grade silicone is used as an illustrative example of a flexible thermoset polymer. The method includes obtaining or creating a mold (335) (block 305), filling the mold (335) with polymer (340) and then curing the polymer (block 310). The cured polymer (340) is then removed from the mold (335) (block 315). Because of the substantial amount of elasticity of the polymer (340), the mold (335) can have substantial undercuts (negative draft angles) without trapping the molded silicone piece (340). During removal, the polymer (340) deforms and allows larger cross section portions to be extracted through narrower openings. As discussed above, using silicone to form the polymer has a number of advantages including flexibility when cured, biocompatibility, chemical inertness, low surface energy, and good electrical insulation. Additionally, silicone surfaces are tacky. This can provide some amount of adhesion between the wires and the grooves that assists in holding the wires in place prior to permanent encapsulation.

After removing the polymer (340) from the mold (335), wires (345) can be placed into the grooves (block 320). As discussed above, the wires (345) are inserted through openings that are smaller than the diameter of the wire (345). The shape of the grooves captures the wires (345) and holds them in place during subsequent steps. Although the wires (345) are shown with round cross sections, wires with a variety of other cross-sectional shapes could also be used. The assembly is placed in a form (355) and then encapsulated by depositing an encapsulation layer (350) over the captured wires (block 325). The encapsulation layer (350) locks the wires (345) in place. After curing the encapsulation layer (350), the wire construct (360) is removed from the form (355). The polymer and encapsulation layer (340, 350) can have a variety of thicknesses, depending on the design. The techniques described herein are largely independent of the thickness of the layers.

Although casting is shown as the molding process in FIG. 3, a variety of other molding techniques could be used. For example, liquid injection molding could be used to mold polymer parts with the desired geometry for either the polymer, the encapsulation layer, or both. In many embodiments, the molds are reusable and can be used for bench top fabrication.

As used in the specification and appended claims, the term "flexible" when applied to polymers refers to polymers that meet one or more of the following conditions. First, a flexible polymer is elastic enough to deform when a wire is passed through the narrow mouth of groove formed in the polymer. Second, if a mold with undercut shapes is used, the flexible polymer is elastic enough to be extracted from the mold. Third, a flexible polymer is elastic enough to produce a wire construct with the desired flexibility. Thus, the term "flexible" as applied to polymers is defined by one or more specific functions of the polymer.

FIG. 4 is flowchart with associated cross-sectional diagrams of a method for forming an illustrative flexible wire construct that incorporates a photolithographic process. A mask layer (440) is deposited over a silicone layer (445) (block 405). These layers are supported by a support (450). The mask layer (440) is patterned using photolithography (block 410). In this example, light (455) cures portions of the mask layer (440). Uncured portions of the mask layer (440) are removed to reveal a pattern of features (442) that corresponds to portions of the mask layer (440) that were exposed to the light (block 415).

Silicone (447) is then deposited into spaces between the features (442), cured, and then the mask features (442) are removed (block 420). For example, the mask features (442) may be removed by chemically dissolving the cured mask material. Removal of the mask features (442) creates the grooves in the polymer (470). Wires (460) are placed in the grooves (block 425). The wires (460) are then encapsulated by the deposition of an encapsulation layer (475). The encapsulation layer (475) is then cured (block 430) and the completed wire construct (480) is removed from the support (450) (block 435).

Figure 5A:
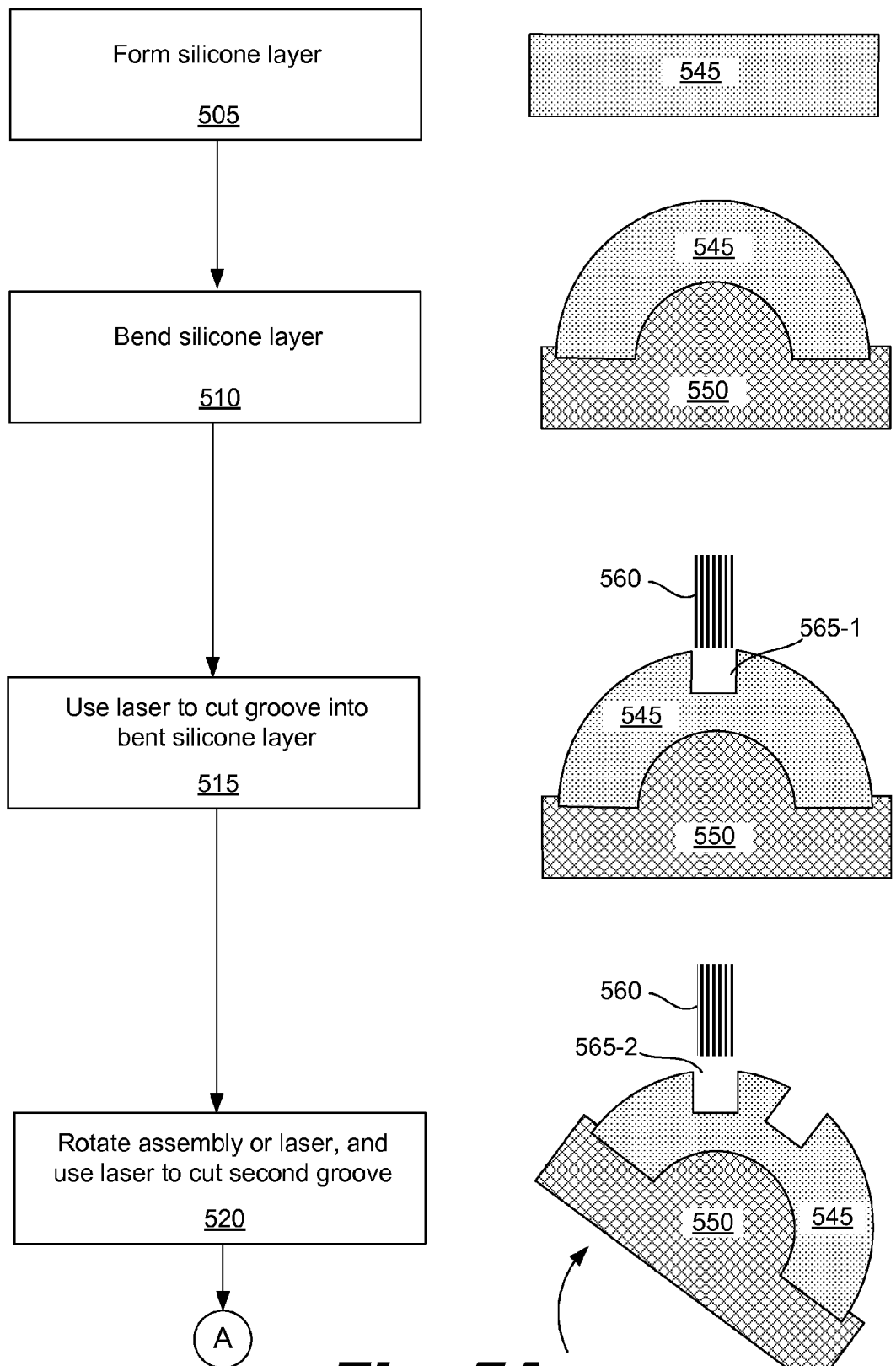
FIGS. 5A and 5B is a flowchart with associated cross-sectional diagrams of an illustrative method for forming a flexible wire construct that incorporates laser forming, according to one example of principles described herein.
Figure 5B:
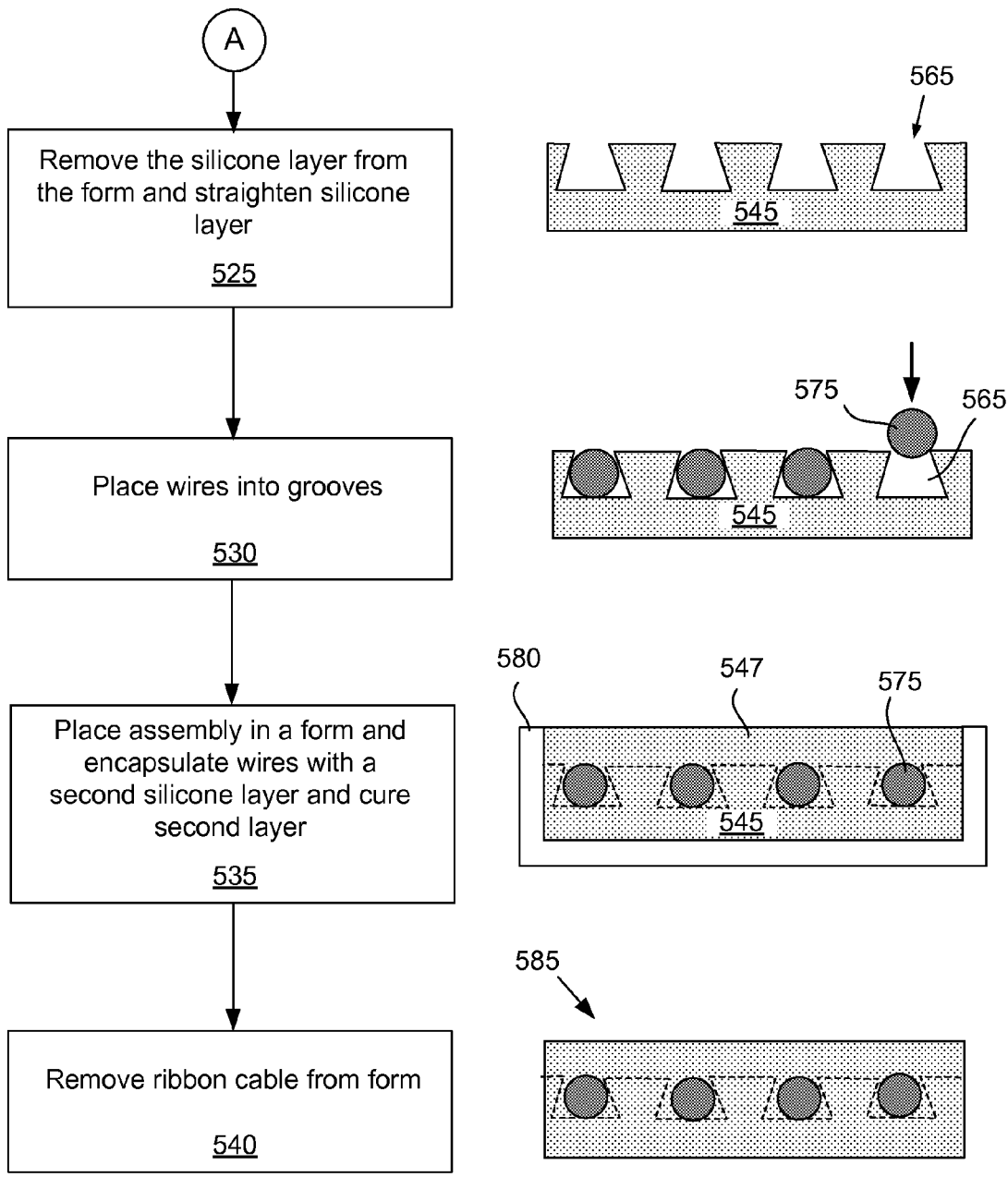

FIGS. 5A and 5B show a flowchart with associated cross-sectional diagrams of an illustrative method that incorporates laser cutting to produce a flexible wire construct. In this method, a cured flexible polymer (545) is formed (block 505). The flexible polymer (545) is then bent to produce tensile strain in an outer surface of the flexible polymer (545) (block 510). This may be done in a variety of ways, including bending the polymer (545) around a form (550).

A laser (560) is then used to cut a groove (565-1) into the bent polymer (545) (block 515). To create other grooves (565), the laser (560) or the bent polymer (545) may be repositioned. According to one example, the form (550) could be rotated to position another portion of the polymer layer (545) under the laser (560). A second groove (565-2) is then created (block 520). The process of repositioning the laser (560) or the bent polymer (545) can be repeated until the desired numbers of grooves (565) are created.

FIG. 5B shows the straightened polymer (545) after it has been removed from the form (550, FIG. 5A) (block 525). The laser cut grooves (565), that were initially rectangular in the bent polymer (545), have become more closed as the polymer (545) was straightened. These grooves (565) form grooves that are suited to receive and capture wires with a diameter or dimension wider that the mouth of the groove. The wires (575) are placed into the grooves (block 530). The grooves (565) hold the wires in place until they are encapsulated. The assembly is placed in a form (580) and an encapsulation layer (547) is deposited over the top of the wires (575) and grooves (565) and then cured (block 535). The completed wire construct (585) is then removed from the form (580) (block 540).

FIG. 6A is a perspective diagram of an illustrative extrusion device (605, 610) for extruding grooved polymers shapes (615). FIG. 6B is a flowchart of a method for forming a flexible wire construct using extruded polymer shapes. An extrusion unit (605) performs mixing and conditioning of input materials to form the polymer material. The input materials may include polymer precursors, colorants, fillers, or other materials. According to one example, the input materials are two-part silicone gumstock. The polymer material is then forced through a die to form the desired grooved polymer (615) (block 620).

The grooved polymer (615) is pulled through a curing unit (610) and is cured (block 625). The curing unit (610) may employ any of a number of techniques to cure the polymer, including heated air, microwaves, a radiant oven, a heated bath, or other appropriate curing techniques. The cured polymer shape (615) exits the curing unit (610). A number of additional blocks can then be performed to prepare the polymer for use. For example, the polymer can be cleaned, measured, and cut to the desired length and with the desired end shape. Wires are then placed into the grooves (block 630) and an encapsulation layer is placed over the wires (block 635). The extrusion system and method described above may have a number of advantages such as low cost and consistent quality in producing large quantities of shaped polymer.

Figure 7:
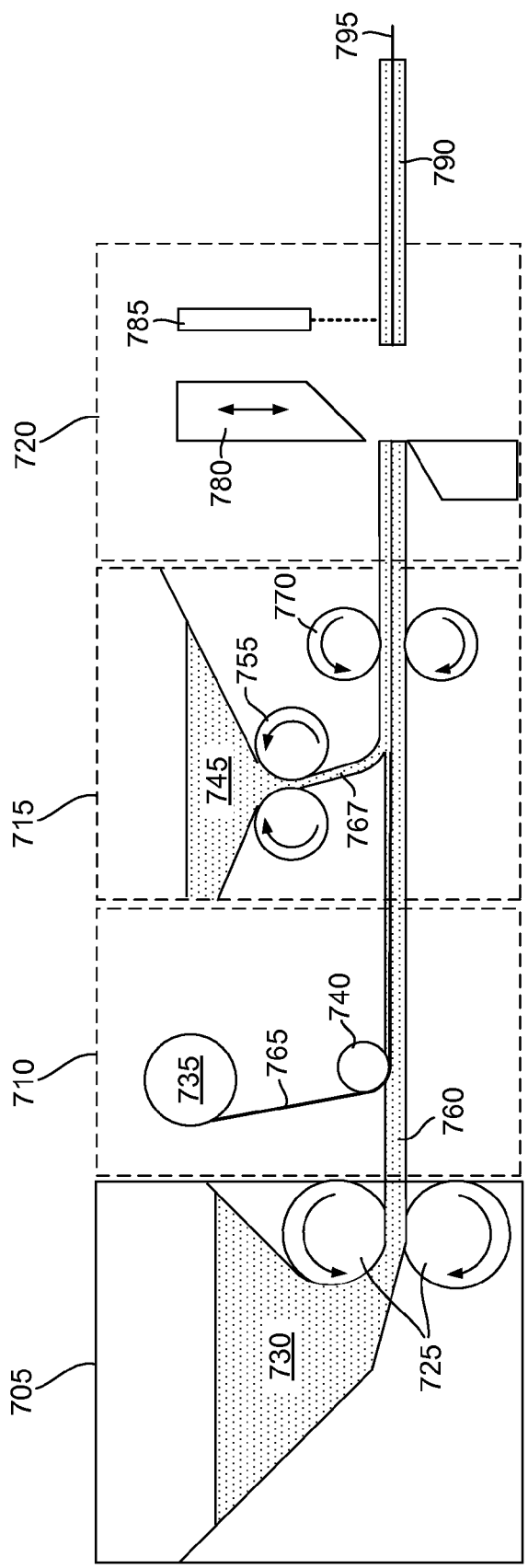
FIG. 7 is a diagram of an illustrative process for manufacturing flexible wire constructs using calendering, according to one example of principles described herein.

FIG. 7 is a diagram of an illustrative automated system and process that begins with raw materials and produces finished wire constructs. In a first module (705), a calendering mechanism takes uncured silicone (730) and passes it between two forming rollers (725) to form a shaped polymer (760). The rollers (725) are shaped to create the desired groove geometries in the polymer (760). In one example, the forming rollers (725) are heated to cure the polymer (760).

The second module (710) deposits the wires (765) from spools (735) into the grooves. For example, rollers (740) could be used to press the wires (765) into grooves. Additionally, a variety of other methods could be used to place the wires (765) in the grooves. For example, a wire bonder could be modified to place the wires (765) in the grooves.

A third module (715) forms and deposits an encapsulating layer (767) over the wires (765) and into the grooves. The upper rollers (755) form the encapsulation layer (767) from a reservoir of uncured silicone (745) and a second set of rollers (770) press the encapsulation layer (767) into place and cure it. The assembly is then passed into a fourth module (720) where it is sectioned and trimmed. In this example, the sectioning of the assembly into desired lengths is performed by a knife (780). The trimming is performed by a laser (785). The trimming exposes the wire ends (795). The wire construct (790) is then ready for post manufacturing blocks and incorporation into an implanted medical device.

The examples shown in FIGS. 3, 4, 5A-5B, 6A-6B, and 7 are only illustrative methods. A variety of other blocks could be added to the methods described above and blocks could be combined or omitted. For example, the calendering mechanism shown in FIG. 7 could be replaced with an extrusion mechanism. In another example, a vacuum or pressure curing process could be used to cure the encapsulating layer to minimize bubbles and unfilled areas of the grooves.

Figure 8A:
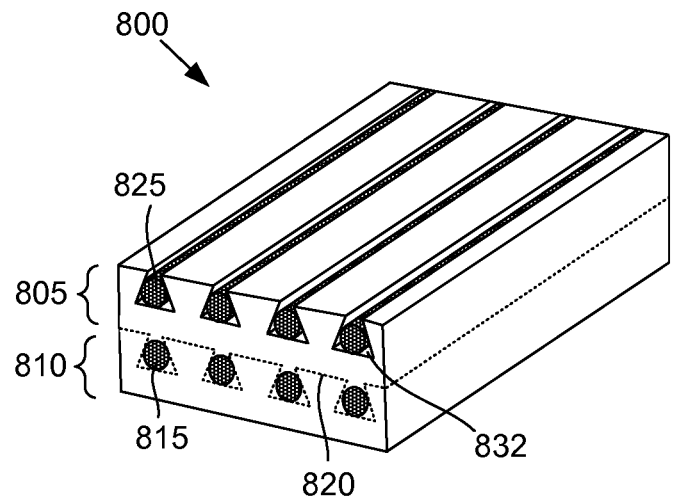
FIG. 8A is a perspective view of an illustrative multilayer wire construct, according to one example of principles described herein.

The illustrative systems and processes described above can be used to form a variety of different flexible wire constructs. FIG. 8A is a perspective view of an illustrative multilayer wire construct (800). This multilayer construct (800) can be formed using any of the techniques described above, a combination of the techniques, or a variety of other techniques. For example, a polymer (810) could be formed using molding, photolithography, laser forming, or other techniques. Wires (815) are then placed into the grooves and an encapsulation layer (805) is deposited over the grooves in the polymer (810). In some cases a mold could be used to simultaneously form grooves (832) in the encapsulation layer (805). The encapsulation layer (805) is then cured. The separation between the polymer (810) and encapsulation layer (805) is shown by the dashed parting line (820). In embodiments where the polymer (810) and the encapsulation layer (805) are formed from different materials, the parting line (820) can be very distinct. In contrast, where the polymer (810) and the encapsulation layer (805) are both formed from silicone, the parting line (820) may be less distinct.

Grooves (832), if not previously formed during molding of upper silicone layer (805), can then be formed using any of the previous described techniques or other suitable techniques. Upper wires (825) are then deposited into the grooves (805) and encapsulated with a third layer of silicone (not shown).

The multilayer embodiment shown in FIG. 8A is only one illustrative example. A variety of other configurations could be formed. For example, the upper and lower wires could be horizontally offset from each other or the wire placement could be in a different shape than the pattern shown.

Figure 8B:
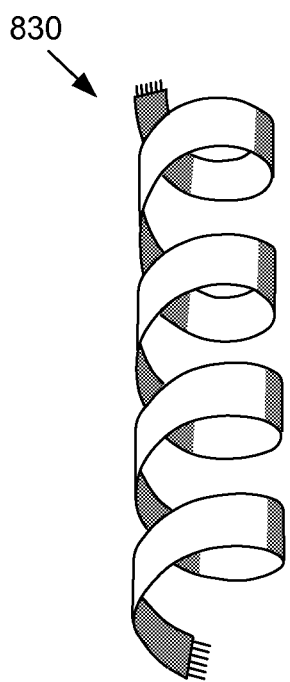
FIGS. 8B and 8C are perspective views of illustrative helical wire constructs, according to one example of principles described herein.

FIG. 8B is a perspective view of an illustrative helical wire construct (830). This helical wire construct (830) could be formed with any of a variety of flexible wire constructs including any of the single or multiple layer examples described above. The helical construct (830) can be formed in a number of ways, including wrapping a flat wire construct around a rod during a portion of the curing process. In other embodiments, an additional layer of silicone could be placed over the helically wrapped wire construct. This additional layer is then cured. After completion of the curing process, the wire construct will maintain its helical shape.

Figure 8C:
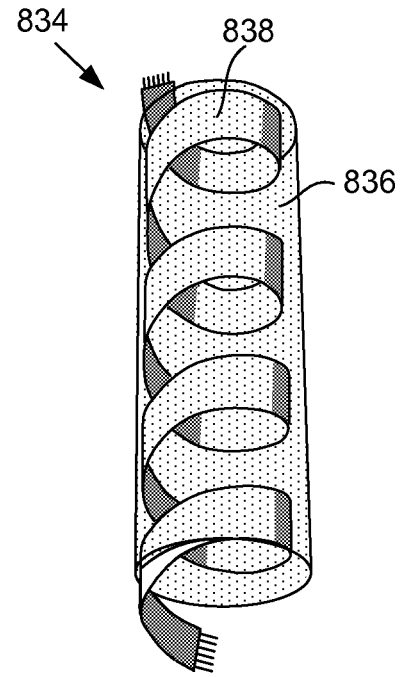

FIG. 8C shows a helical construct (834) that includes a wire construct (838) encapsulated in a flexible polymer body (836). These helical constructs (830, 834) may have a number of advantages including substantially uniform bending stiffness in any direction. Additionally, the helical constructs (834) have advantages related to sustaining and transferring stress during manipulation.

The techniques, processes, and systems are not limited to the illustrative wire constructs described above and can be used in any design where discrete placement of wires is needed. For example, implantable coils and flexible circuitry can be formed by creating grooves, placing wires in the grooves, and then encapsulating the wires using an additional layer.

Figure 9:
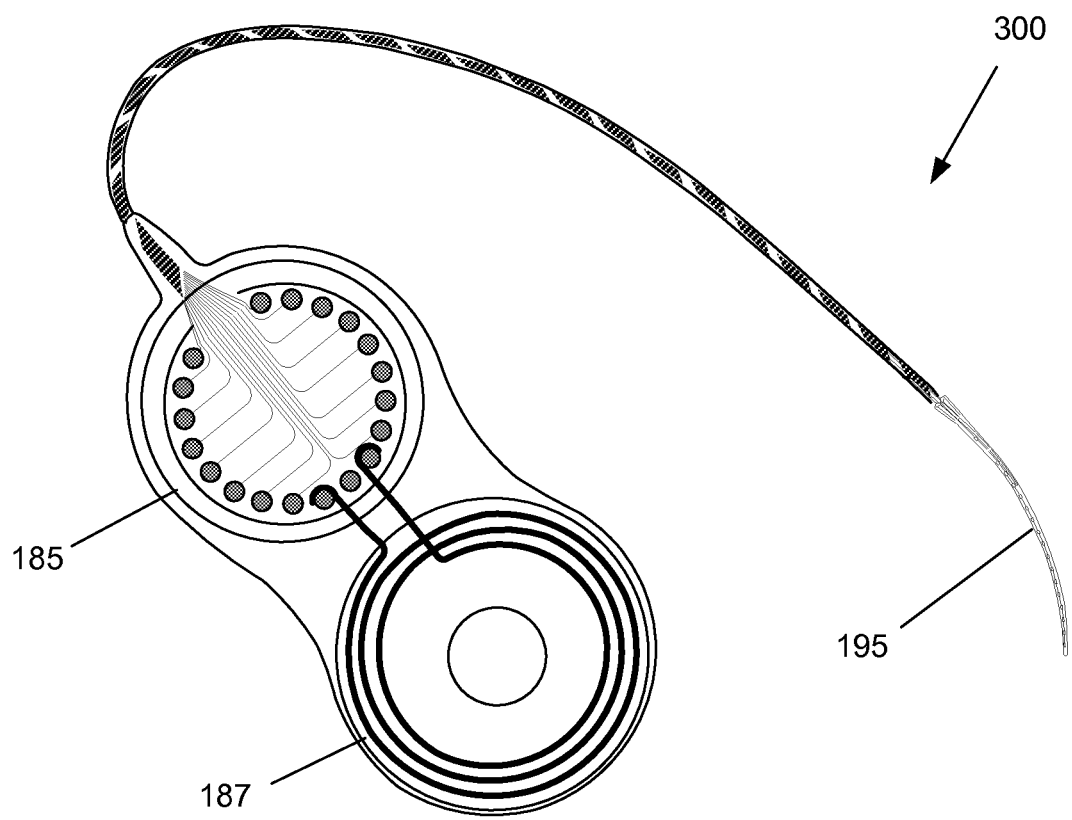
FIG. 9 is a top view of a cochlear implant formed using flexible wire constructs, according to one example of principles described herein.

FIG. 9 is a top view of an illustrative cochlear implant (300) that includes a flexible wire constructs. A first flexible wire construct can be used to route wires from a signal processing unit (185) to electrodes in an electrode array (195). A second flexible wire construct can be used to create the antenna (187). The antenna (187) can be formed using principles discussed above.

Figure 10F:
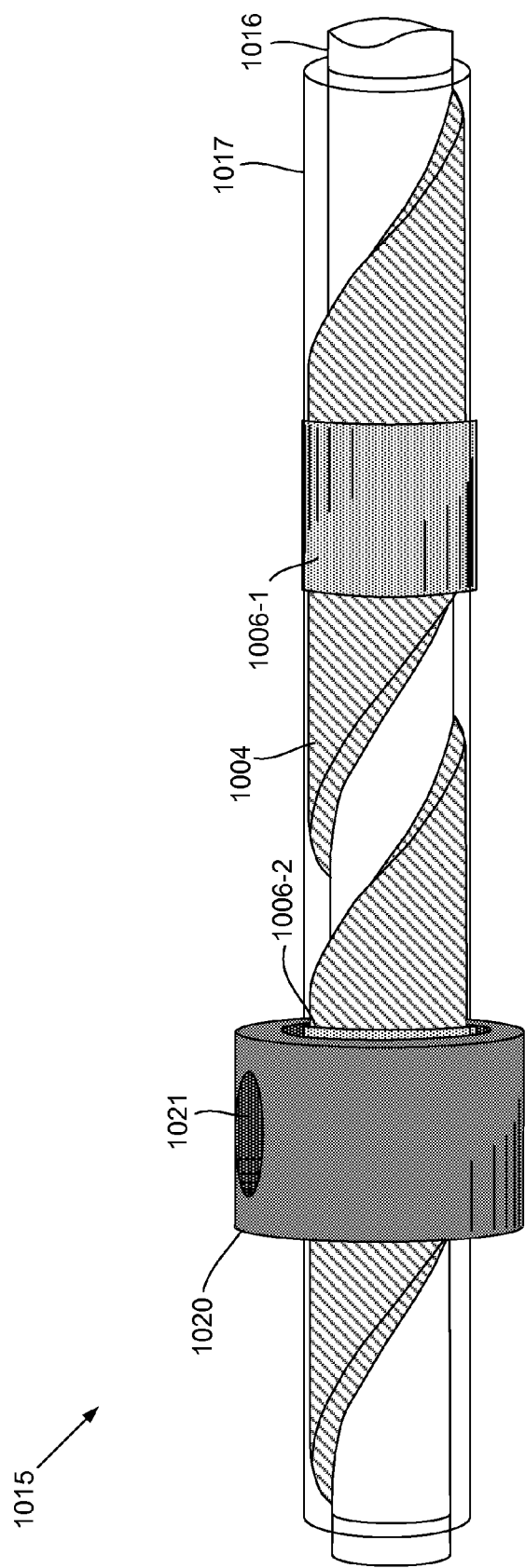

FIGS. 10A-10G show illustrative steps in forming a cochlear implant (300 FIG. 9) which includes a flexible wire construct (1000). FIG. 10A is a top view of the flexible wire construct (1000) that includes a circular portion (1005), a body portion (1010) and a triangular portion (1015). The flexible wire construct (1000) is formed using methods and principles described above. For example, the construct (1000) may be formed by creating grooves in a silicone layer, placing wires in the grooves, and then depositing an overcoat on the grooved surface to lock the wires in place. Although the implementation shown in FIG. 10A has a single wiring layer, the construct (1000) may have two or more wiring layers for more compact routing of the wires.

The circular portion (1005) fans out the wires (1004) to connect with a radial array of contacts (1002). The contacts (1002) may be formed and joined to the flexible wire construct (1000) in a number of ways. For example, the contacts (1002) may be separate elements that are at least partially embedded in the flexible wire construct (1000). The wires (1004) are then bonded to the contacts (1002) using any of a number of techniques, including resistance welding and laser welding. In other embodiments, the contacts (1002) may be formed from the wires (1004) themselves. For example, the ends of the wires (1004) may be melted to form a ball, which is then flattened into a contact. In other implementations, there are no contacts (1002) in the flexible wire construct (1000). Instead the wires (1004) extend from the flexible wire construct (1000) and are directly attached to pins or contacts on the signal processor (185, FIG. 9).

The body portion (1010) of the flexible wire construct (1000) routes the wires (1004) from the signal processor (185, FIG. 9) to the triangular portion (1015). The body portion (1010) is flexible and can be formed into any of a number of shapes to facilitate routing, obtain the desired form factor or increase the flexibility of the body portion. In this example, the wires (1004) in the body portion (1010) are illustrated as being straight and parallel.

The triangular portion of the flexible wire construct (1000) routes wires (1004) to a linear array of flexible pads (1006). These flexible pads (1006) may be formed from a range of flexible conductive materials. For example, the flexible pads may be formed from platinum or platinum alloys. To create the pads, a platinum foil may be laser machined to form individual pads, or a connected array of pads. The wires (1004) are then attached to the pads. In one embodiment, the wires (1004) in the flexible wire construct (1000) may be embedded using a wire bonding machine.

FIG. 10B shows the body portion (1010) coiled to form a helical construct that has substantially uniform bending stiffness in any perpendicular orientation and can be longitudinally extended with minimal force. As discussed above, this may provide a number of advantages including reducing stress on electrical interconnections and allowing for motion and growth of the patient. FIG. 10C shows the coiled body portion (1010) encapsulated with a flexible overcoat (1011) to preserve its coiled shape. The triangular portion (1015) has not yet been coiled.

FIG. 10D shows the triangular portion (1015) coiled around a cylindrical element (1016). The flexible pads (1006) are also coiled around the cylindrical element (1016) to create conductive bands that encircle the coiled triangular portion (1015) of the wire construct (1000). As explained below, the flexible pads (1006) will serve as connection points for electrodes.

The cylindrical element (1016) can remain in place or be removed. For example, the cylindrical element (1016) may be a PTFE tube which remains in place to serve as a lumen liner. In other embodiments, the cylindrical element (1016) may be configured to be removed. The resulting void can be used as a lumen or filled with an encapsulant.

FIGS. 10E and 10F show ring electrodes (1020) attached to the wire construct (1000). The term "ring electrode" refers to any toroidal shape or partially toroidal shape. For example, C-shaped electrode or other similar partially open electrode is a ring electrode. As shown in FIG. 10E, an overcoat (1017) is placed over the triangular portion (1015) of the wire construct. The overcoat (1017) fills voids and holds the triangular portion (1015) in the cylindrical shape. In one implementation, the overcoat (1017) does not cover the exterior surface of the flexible pads (1006, FIG. 10D). In another implementation, the overcoat (1017) covers the entire surface of the triangular portion (1015) and is selectively removed to expose the flexible pads (1006). In this implementation, the cylindrical element (1016) remains in place at the center of the wire construct (1000).

Ring electrodes (1020) are electrically connected to the wire construct and are in direct contact with biological tissues and fluids. The ring electrodes receive electrical impulses and transmit those impulses to the biological tissues. The ring electrodes (1020) are sized so that they slip over the coiled triangular portion (1015) and overcoat (1017), with one ring electrode (1020) positioned over each of the flexible pads (1006, FIG. 10D). The ring electrodes (1020) are then electrically connected to the pads (1006, FIG. 10D) and mechanically connected to the wire construct (1000). The ring electrodes (1020) could be formed from a variety of materials, including platinum alloys. The surface of the ring electrodes (1020) could be coated or activated to increase the charge transfer capability of the electrodes.

FIG. 10F is an expanded view of a portion of the wire construct (1015) that shows the wires (1004) wrapped around the cylindrical element (1017). Two flexible pads are shown (1006-1, 1006-2) wrapped over the triangular portion (1015). A ring electrode (1020) has been placed over one pad (1006-2). The ring electrode (1020) includes a through hole (1021) on its perimeter. The hole (1021) can be used to attach the electrode (1020) to the underlying pad (1006-2). For example, a laser welder could use the hole (1021) to create a welded joint at the bottom of the hole that connects the electrode (1020) to portions of the pad (1006-2) exposed by the hole. This is only one illustrative technique for attaching ring electrodes (1020) to the flexible pads (1006). Other techniques could also be used. For example, the pads (1006) may be slightly wider than the ring electrodes (1020). When an electrode (1020) is placed over a pad (1006), the sides of the electrode (1020) could be welded to the exposed portions of the flexible pads (1006).

Figure 10G:
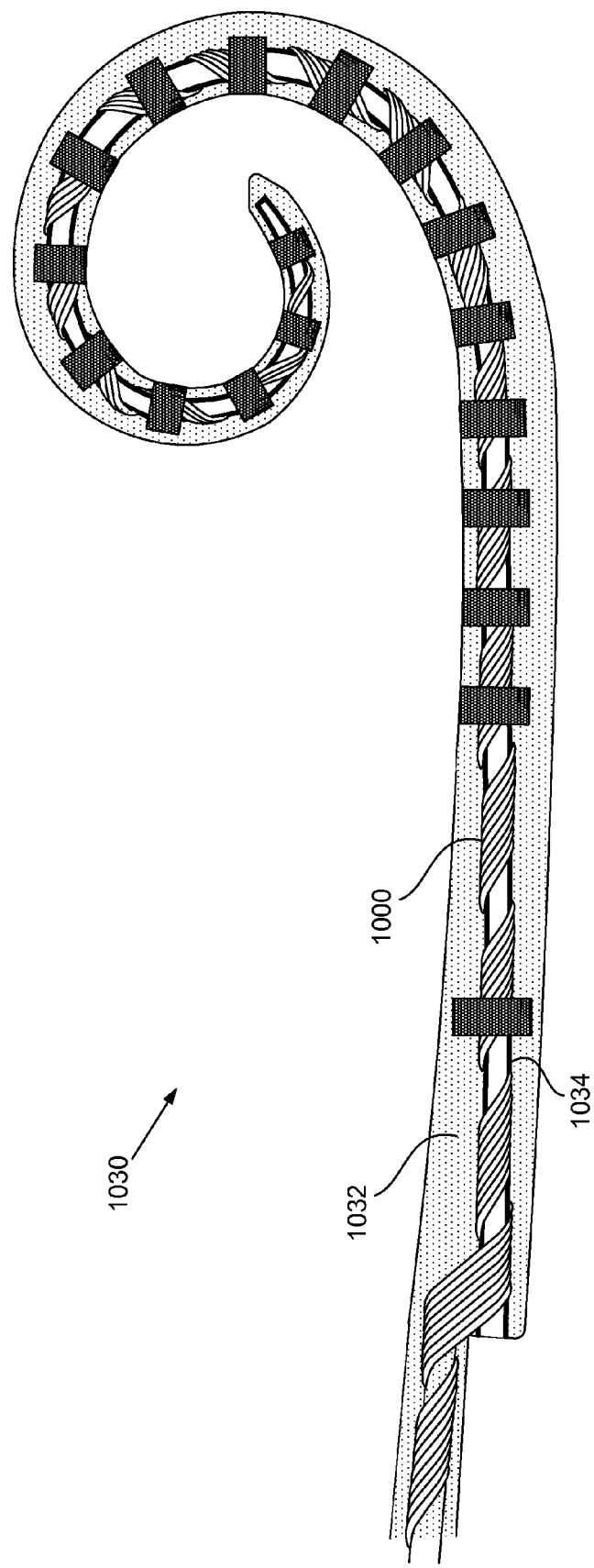

FIG. 10G shows a completed cochlear electrode (1030) that includes a flexible wire construct (1000). To form the completed cochlear electrode (1030), the flexible wire construct (1000) is placed in a spiral mold and encapsulated. The additional encapsulation (1032) fills the mold and holds the flexible wire construct (1000) in the desired geometric configuration. In this example, the wire construct (1000) has been wrapped around a lumen liner (1034) that has been retained in the cochlear electrode (1030). During insertion, a stiffening element can be inserted into the lumen created by the lumen liner (1034) to facilitate control and placement of the cochlear electrode (1030).

Figure 11A:
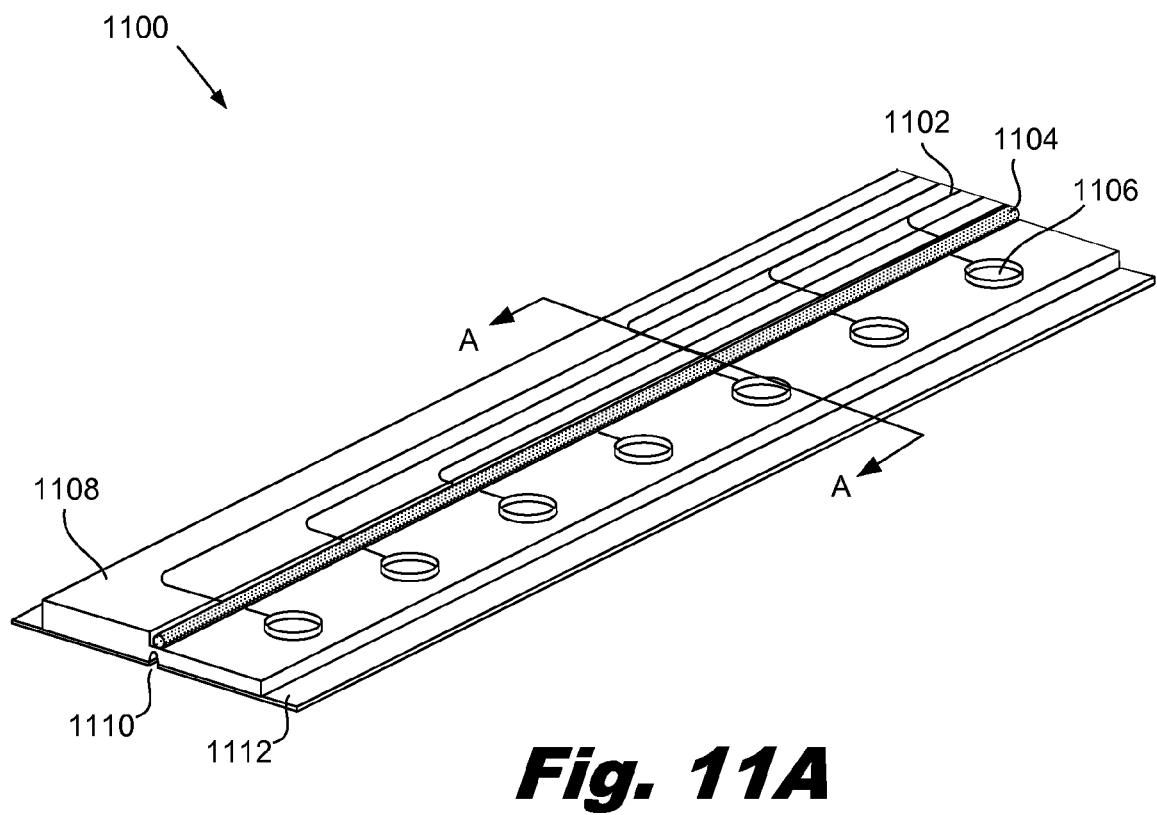
FIG. 11A is a partial perspective view of construction of an electrode array using a flexible wire construct, according to one example of principles described herein.

The electrode array (195, FIG. 9) and methods described above for forming the wire construct (1000, FIG. 10A) are only illustrative examples. A variety of other construct geometries and techniques could also be used. FIG. 11A is a perspective view of an distal portion of an electrode array (1100). In this embodiment, a thermoset polymer (1108), such as silicone, is deposited on a thermoplastic substrate (1112). Thermoplastics include acrylates, polyamides, polyethylene, polyketones, polystyrenes, polyurethanes, polyvinyls, and other plastics. For example, the thermoplastic substrate could be a polyimide, liquid crystal polymer (LCP), parylene, or polytetrafluoroethylene.

As described above in FIGS. 1A-8C, grooves (1102) are formed in the thermoset polymer (1108) to control wire routing. Cavities (1106) are also formed in the thermoset polymer (1108). These cavities (1106) are adapted to receive electrodes. In this example, the corresponding electrodes would be disks sized to fit in the cavities (1106). Alternatively, the cavities and electrodes could have any suitable shape.

In most cases, the thermoplastic substrate (1112) will be significantly more rigid than the thermoset polymer (1108) at ambient temperatures. Consequently, the thermoplastic substrate (1112) can be modified to control the folding behavior of the electrode array (1100). For example, portions of the thermoplastic may be thinned, scored, or removed to facilitate precision folding of the electrode array. In this implementation, a trench (1110) is formed down the center of the thermoplastic substrate (1112). The trench (1110) facilitates folding of the electrode array in subsequent steps. A strain relief element (1104) is placed down the center of the electrode array. As described below, the wires pass over the strain relief element (1104) as they pass down the grooves (1102) to the cavities (1106) where the electrodes will be placed.

FIG. 11B is a method for forming an electrode array that includes a wire construct (1100). A flowchart is shown on the left side of the figure and corresponding cross sectional diagrams are shown on the right side of the figure. The initial cross sectional view is taken along line A-A in FIG. 11A. As discussed above with respect to FIG. 11A, a thermoset plastic (1108) is deposited on a thermoplastic substrate (1112) and grooves (1102) are formed in the thermoset plastic (1108) (block 1150). In this implementation, two distinct sets of grooves (1102-1, 1102-2), separated by the strain relief element (1104), are formed. As discussed above, the grooves (1102-1, 1102-2) have a mouth that is narrower than a width of a deeper portion of the grooves. Additionally, a trench (1110) is formed in the thermoplastic (1112) and an electrode (1114) is placed in the cavity (1106, FIG. 11A) of the thermoset plastic. The initial cross section is a multilayer wire construct with a lower layer of signal wires (1116) already in place and encapsulated in the thermoset polymer (1108).

A wire (1118) is placed in the grooves (1102-1, 1102-2), over the strain relief element (1104) and is connected to the electrode (1114) and encapsulated (block 1155). The passage of the wire (1118) over the strain relief element (1104) creates a strain relief geometry (1120) in the wire (1118). As discussed above, the wire (1118) has a larger cross-sectional dimension than the mouth of the grooves (1102-1, 1102-2) and is retained in the grooves (1102-1, 1102-2) until an overcoat is deposited to lock the wire (1118) into the groove (1102-1, 1102-2).

The strain relief element (1104) is removed and the wire construct (1100) is folded along the trench (1110) (block 1160). The strain relief geometry (1120) in the wire (1118) provides slack so that the wire (1118) is not damaged when the wire construct (1100) is folded. The construct (1100) is folded so that the two surfaces of the thermoplastic substrate (1112) come into contact and are bonded together (block 1165). These two surfaces can be bonded to each other using a number of methods, including melting the thermoplastic (1112) to fuse the surfaces or using an adhesive between the surfaces.

An encapsulant (1124) is deposited over the wire construct (1100) (block 1170). This produces an electrode array (1130) in a near net shape. The encapsulant (1124) may include a variety of features, including a lumen (1122). In this implementation, the lumen (1122) is formed in the encapsulation (1124) over the wire construct (1100). However, the lumen (1122) could be formed in a variety of locations, including between the two thermoplastic layers (1112).

Overall shape of the electrode array (1130) can be adjusted after molding by heating the thermoplastic substrate (1112) above its glass transition temperature. The thermoplastic substrate (1112) is cooled while holding the electrode array (1130) in the desired shape. After cooling, the thermoplastic substrate (1112) will tend to remain in the desired shape and will exert forces on the electrode array (1130) that will tend to draw it into the desired shape. For example, if the electrode array (1130) is a cochlear electrode array, the desired shape may be a spiral that follows the internal shape of a cochlea. The electrode array (1130) can be heated so that the thermoplastic becomes pliable. The electrode array (1130) is then shaped into a spiral. The spiral may be slightly tighter than the actual shape of the cochlear duct. This compensates for forces exerted by the thermoset plastic and allows for some amount of relaxation. The assembly is cooled and the thermoplastic (1112) tends to retain the tighter spiral shape while the thermoset plastic (1108, 1124) tends to force the spiral open. The final shape of the electrode array (1130) is a result of the balance between these two forces and will be predictably more open than the tighter spiral shape.

Figure 11C:
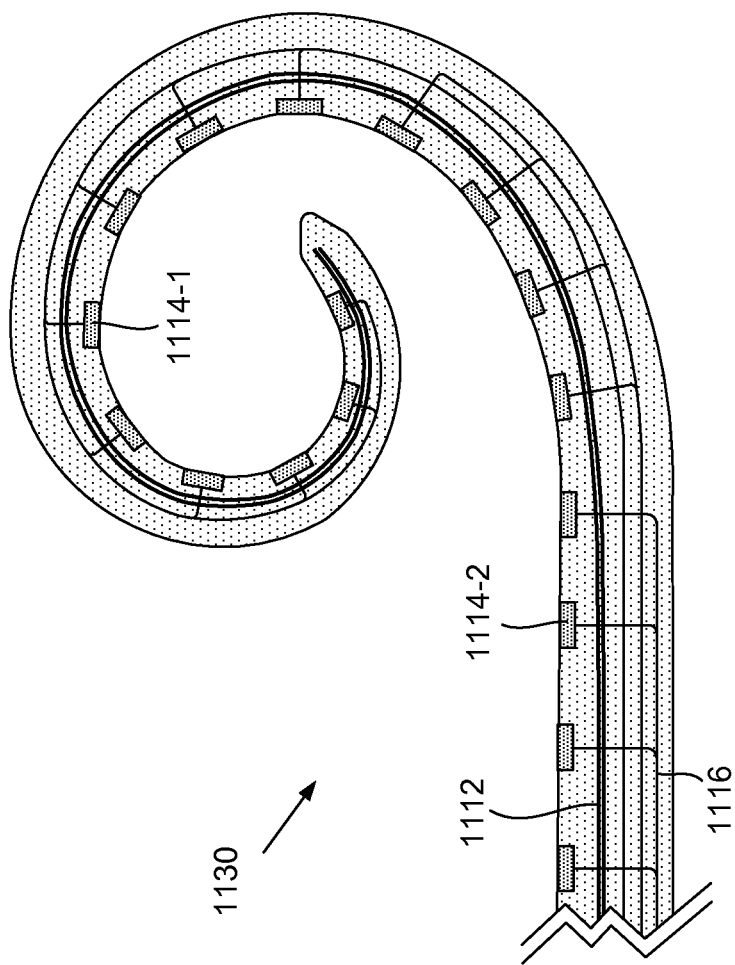
FIG. 11C is a side view of an electrode array prepared according to the method illustrated in FIG. 11B, according to one example of principles described herein.

FIG. 11C shows the distal portion of a cochlear electrode (1130) formed using the method described above. In this example, there are three wiring layers on one side of the folded thermoplastic substrate (1112). The first wiring layer routes wires (1116) to the more distal electrodes (1114). The second and third wiring layers route wires (1116) to the remaining, more proximal electrodes. The thermoplastic substrate (1112) acts as a spiral stiffening element and, in the absence of exterior forces, holds the cochlear electrode in the desired spiral shape. The wires (1116) pass around the thermoplastic substrate (1112) to the electrodes (1114) on the opposite side. No lumen is shown in this cochlear electrode (1130).

Figure 12A:
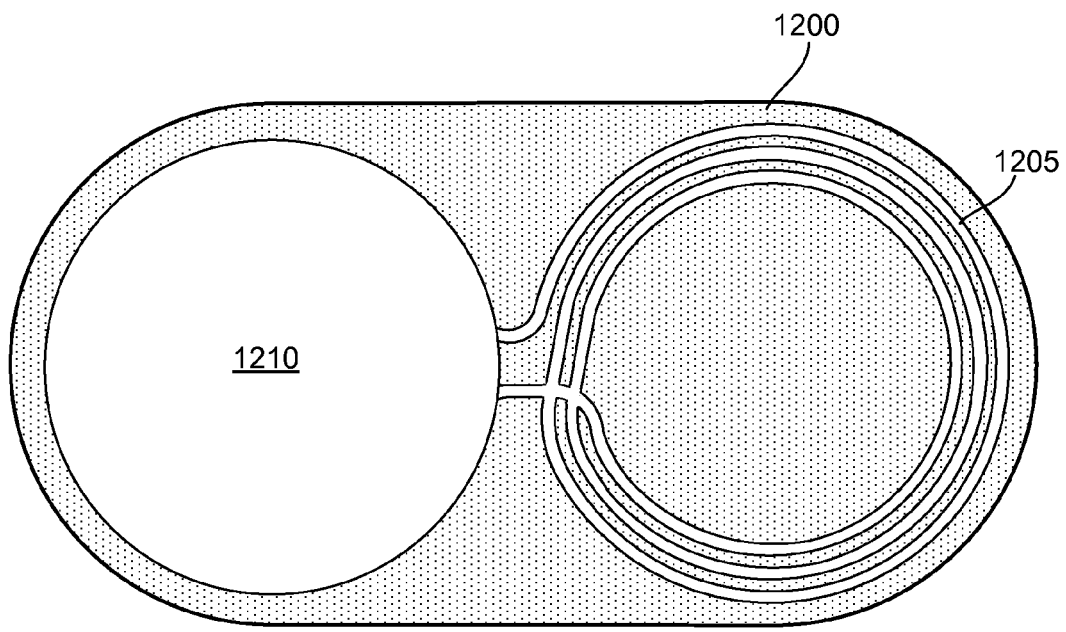
FIG. 12A is a top view of a flexible polymer with spiral channel, according to one example of principles described herein.
Figure 12B:
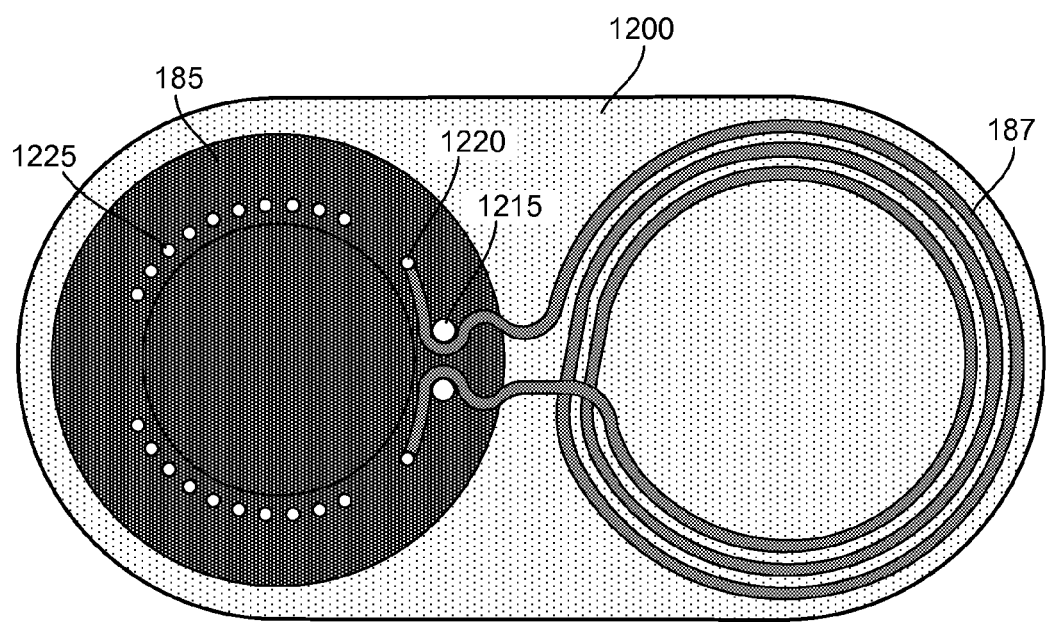
FIG. 12B is a top view of an antenna formed by laying a wire in the spiral channel, according one to example of principles described herein.

A variety of other wire constructs can be formed using the systems, methods, and principles described above. For example, the antenna (187) shown in FIG. 9 can be formed using the principles described above. FIG. 12 shows an illustrative example of the creation of an antenna using a flexible wire construct. FIG. 12A shows a polymer (1200) with a spiral shaped groove (1205) and a cavity (1210) configured to receive a signal processor (185, FIG. 12B). The spiral groove (1205) intersects itself at several locations so that the interior loop of the wire in the spiral groove (1205) can be brought outside of the spiral groove (1205) and attached to the appropriate terminal of the signal processor (185, FIG. 12B).

FIG. 12B shows a signal processor (185) placed in the cavity (1210, FIG. 12A) and an antenna wire (187) placed in the spiral groove (1205, FIG. 12A). To accommodate the intersections, the antenna wire (187) can be insulated along its length. The ends of the antenna wire (187) pass out of the groove (1205, FIG. 12A) to pass around anchor pegs (1215) and electrically connect to signal pins (1220). A cochlear electrode assembly, such as those shown in FIG. 10G and FIG. 11C, can be attached to the remaining pins (1225) to form a cochlear implant similar to that illustrated in FIG. 9.

Figure 13A:
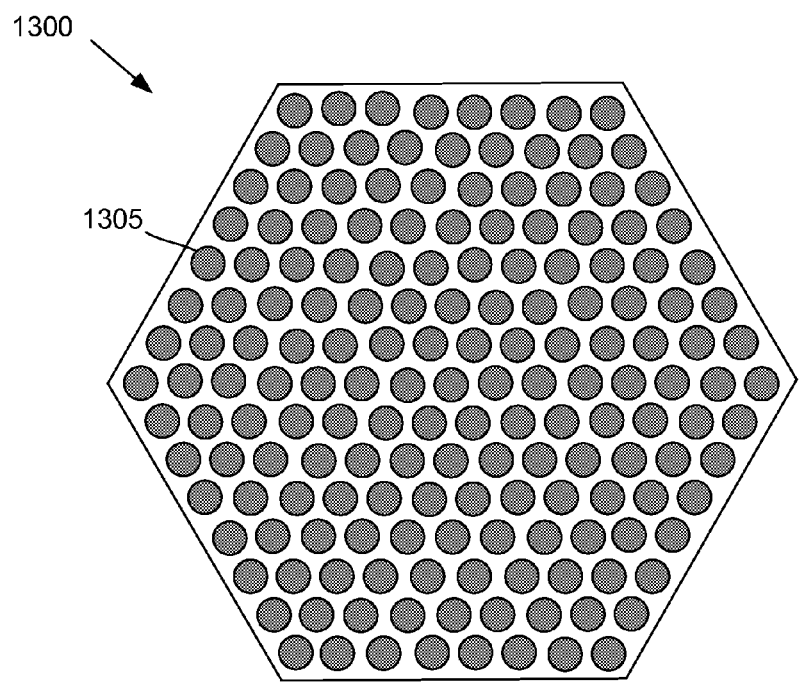
FIGS. 13A and 13B are views of a high density two dimensional electrode array, according to one example of principles described herein.
Figure 13B:
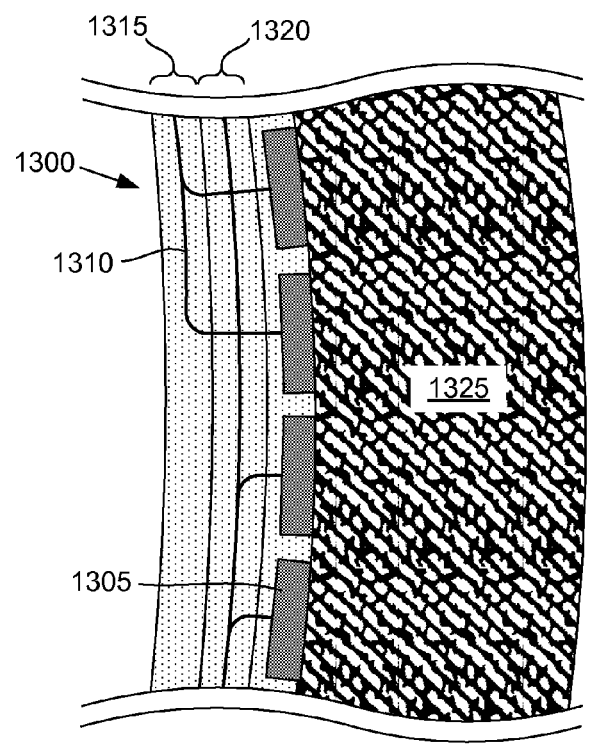

In addition to cochlear implants, the flexible wire constructs can be used in a variety of other devices. FIGS. 13A and 13B show a two dimensional electrode array (1300) that has been formed according to the principles discussed above. The ability to precisely route signal wires and package those signal wires in a multilayer wire construct allows a very dense electrode array to be created. The electrode array is brought into proximity with nerve endings in the target tissue. For example, the two dimensional electrode array may be used in neural prosthetics for artificial vision, artificial limbs, spiral cuff electrodes and brain interfaces.

FIG. 13A shows a two dimensional electrode array (1300) which can be used as a retinal implant. In this example, the two dimensional electrode array is a hexagonal device that has closely packed electrodes (1305). FIG. 13B shows a cross sectional view of a small portion of the electrode array (1300) positioned over the retina (1325). The multiple wiring layers (1315, 1320) of the electrode array (1300) are illustrated in FIG. 13B. Each wiring layer (1315, 1320) routes signal wires (1310) from a processor to a designated group of electrodes (1305). These wiring layers (1315, 1320) can be created using the principles described above. Although only two wiring layers are shown, the electrode array (1300) could have any number of wiring layers that are appropriate to route signals to the electrodes (1305).

In conclusion, ribbonized wire constructs, methods, and systems described above provide more accurate and rapid placement of wires within a wire construct by forming grooves in a polymer to hold the wires in place. The use of elastic polymers can allow for very cost effective molding and shaping operations of the grooves.

In one aspect, a method for forming a wire construct may include forming a groove in a polymer having a mouth that is narrower than a width of a deeper portion of the groove and placing a substantial length of a wire in the groove. The wire may have any cross section, including cross sections that have a larger dimension than the mouth of the groove. For example the wire may have a round cross section with a larger diameter than the mouth of the groove.

In one aspect, the wire may have a smaller diameter than the mouth of the groove but may be formed into a coil or undulating shape such that the wire geometry has a dimension that is larger than the mouth of the groove.

In any of the methods or structures described herein, the groove or grooves may be formed in any of a number of ways, including by depositing uncured polymer into a mold and curing the polymer, extruding a polymer, photolithographic patterning of a mask to cure portions of the mask, laser cutting, calendaring or any combination of those or other methods. The groove or grooves may have any of a variety of shapes, including a dovetail cross section. In one aspect, the multiple grooves are formed in the polymer. These multiple grooves may be straight, parallel and/or nonlinear.

A portion of the wire may be placed in the grooves using any of a variety of techniques, including manually, using a roller, or other suitable technique. In some embodiments, the wires may be placed into the grooves using automated techniques. In one aspect, an encapsulant or additional polymer layer can be deposited over the polymer and wire. The wire construct may have a single layer or multiple layers, with each layer including grooves and wires.

In one aspect, the overall wire construct may be formed into any of a variety of shapes, during or after construction. For example, the wire construct may be flat, tubular, curved or may be formed into coiled helical shape.

In one aspect, the wire construct may include forming multiple grooves in the polymer, placing a first a first length of the wire in a first groove, placing a second length of wire in a second groove and forming a strain relief geometry in the wire between the first length and second length. The strain relief may be formed in any of a number of ways including placing a curved structure between the first groove and the second groove and passing the wire over a surface of the curved structure.

In one aspect, a first end of the wire may be attached to a first electrical contact and a second end of the wire may be attached to a second electrical contact.

In some implementations, the polymer and wire may be folded to form a multilayer circuit. Optionally, all or a portion of the polymer may be deposited on a thermoplastic substrate. In some implementations, the thermoplastic substrate can be notched or include a trench to control folding of the substrate. In one example, the method includes at least one of: folding the thermoplastic substrate and polymer such that two surfaces of the thermoplastic substrate contact each other; and bonding the two contacting surfaces of the thermoplastic substrate to each other. Optionally, the thermoplastic substrate may be heated above a glass transition temperature of the thermoplastic substrate and forming into a predetermined shape. The thermoplastic substrate is then cooled below the glass transition temperature while holding the thermoplastic substrate in the predetermined shape. For example, the predetermined shape may correspond to a shape of a cochlear duct. In other examples, the thermoplastic substrate may be used as a temporary support used during construction of the implantable device and may be removed after it has fulfilled its purpose.

Additionally or alternatively, a multilayer wire construct may include a first flexible wire construct adhered to a second flexible wire construct. In one aspect, the first electrical contact and the second electrical contact may include a flexible conductive contact that is wrapped around the cylindrical body. The flexible conductive contact may serve as an electrode or a separate ring electrode may pass over the flexible conductive contact and be electrically attached to the flexible contact.

In one aspect the method may include attaching the first electrical contact to a via of a hermetically sealed electronics package.

In any of the methods or structures described herein, a lumen may be formed through the polymer, with the lumen configured to receive a stylet. In other implementations, the lumen may be absent.

In any of the methods or structures described herein, the wire construct may include a plurality of grooves and a plurality of wires, in which first ends of the wires are attached to signal generating electronics and second ends of the wires are connected to an electrode array. The electrode array may have any of a variety of configurations. For example, the electrode array maybe a linear array of electrodes in a cochlear lead or a two dimensional array of electrodes in a neural implant. In other embodiments, the wires may not be connected to an array of electrodes but may serve other purposes. For example, the groove may be formed in a planar spiral and a wire placed in the groove to form an antenna. The first and second ends of the wire are electrically coupled to vias of a hermetically sealed electronics package.

In one aspect, a multilayer implantable device includes a first polymer comprising a first plurality of grooves and a first plurality of wires placed within the first plurality of grooves. A first array of electrodes is partially embedded in the first polymer, the first plurality of wires connected to the first array of electrodes. A second polymer is deposited over the first polymer to hold the first plurality of wires in the first plurality of grooves, the second polymer comprising a second plurality of grooves. A second plurality of wires is placed within the second plurality of grooves connected to the second array of electrodes.

In another aspect, an implantable device includes a thermoplastic substrate with a thermoset polymer deposited on the thermoplastic substrate and a plurality of wires passing through the thermoset polymer, the plurality of wires connected to a plurality of stimulating electrodes partially embedded in the thermoset polymer such that at least one surface of each of the stimulating electrodes is exposed. In yet another aspect of the invention, an implantable device may include an array of electrodes, a signal generator, and a helical multilayer wire construct defining a lumen through at least a portion of the construct and configured to receive a stiffening element, the helical multilayer wire construct electrically connecting the array of electrodes to the signal generator. The array of electrodes may include ring electrodes disposed over the construct, in which each electrode in the array of electrodes is electrically coupled to a wire within the construct.

The preceding description has been presented only to illustrate and describe embodiments and examples of the principles described. This description is not intended to be exhaustive or to limit these principles to any precise form disclosed. Many modifications and variations are possible in light of the above teaching.

What is claimed is:

1. A method for forming a wire construct comprising:
   providing a polymer;
   in the polymer, forming a groove having a mouth that is narrower than a width of a deeper portion of the groove;
   placing a substantial length of a wire in the groove, the wire having a larger cross-sectional dimension than the mouth of the groove; and
   depositing an encapsulant over the polymer.

2. The method of claim 1, in which forming the groove comprises at least one of: depositing an uncured polymer into a mold and curing the polymer; extruding the polymer; and laser cutting the groove in cured polymer.

3. The method of claim 1, in which forming the groove comprises:
   photolithographically patterning a mask to cure portions of the mask; and
   removing uncured portions of the mask and depositing the polymer into the mask.

4. The method of claim 1, further comprising folding the polymer and wire to form a multilayer circuit.

5. The method of claim 1, further comprising depositing at least a portion of the polymer on a thermoplastic substrate.

6. The method of claim 5, further comprising notching the thermoplastic substrate to control folding of the polymer.

7. The method of claim 5, further comprising:
   folding the thermoplastic substrate and polymer such that two surfaces of the thermoplastic substrate contact each other; and
   bonding the two contacting surfaces of the thermoplastic substrate to each other.

8. The method of claim 5, further comprising:
   heating the thermoplastic substrate above a glass transition temperature of the thermoplastic substrate;
   forming the thermoplastic substrate into a predetermined shape; and
   cooling the thermoplastic substrate below the glass transition temperature while holding the thermoplastic substrate in the predetermined shape.

9. The method of claim 8, in which the predetermined shape corresponds to a shape of a cochlear duct.

10. The method of claim 1, further comprising:

forming a second groove in the polymer;
placing a second length of the wire in the second groove; and
forming a strain relief geometry in the wire between the first length and the second length.

11. The method of claim 1, further comprising forming a lumen through the polymer, the lumen configured to receive a stylet.

12. The method of claim 1, further comprising a plurality of grooves and a plurality of wires, in which first ends of the wires are attached to signal generating electronics and second ends of the wires are connected to an electrode array.

13. The method of claim 1, in which the groove is formed in a planar spiral, the wire is placed in the groove to form an antenna, and the first and second ends of the wire are electrically coupled to vias of a hermetically sealed electronics package.

14. The method of claim 1, further comprising forcing apart edges of the mouth of the groove to allow the wire, having a larger cross-sectional dimension than the mouth of the groove, to pass into the groove and be placed therein.

15. A flexible wire construct comprising:
a thermoset polymer having a surface that defines a plurality of grooves, each groove having a non-linear zig-zag pattern along a length of the surface, each groove with a mouth that is narrower than a width of a deeper portion of the groove; and
a wire having a larger cross sectional dimension than a width of the groove mouth disposed within each groove.

16. The construct of claim 15, further comprising an encapsulant deposited over the polymer and wires.

17. The construct of claim 15, in which the wire is a coiled wire.

18. The construct of claim 15 in which the zig-zag pattern of the grooves formed in the polymer is non-uniform, each groove having a unique zig-zag shape.

19. The construct of claim 15, in which nonlinear routing of the multiple wires increases the longitudinal stretchability of the wire construct.

20. The construct of claim 15, in which the wire construct has a coiled helical shape.

21. The construct of claim 15, further comprising
a strain relief geometry in the construct between a first length of wire in a first groove and a second length of wire in a second groove.

22. A multilayer implantable device comprising:
a first polymer comprising a first plurality of grooves;
a first plurality of wires placed within the first plurality of grooves;
a first array of electrodes partially embedded in the first polymer, the first plurality of wires connected to the first array of electrodes;
a second polymer deposited over the first polymer to hold the first plurality of wires in the first plurality of grooves, the second polymer comprising a second plurality of grooves; and
a second plurality of wires placed within the second plurality of grooves;
a second array of electrodes, the second plurality of wires connected to the second array of electrodes.

* * * * *